(12) United States Patent
Moriconi et al.

(10) Patent No.: US 8,906,946 B2
(45) Date of Patent: Dec. 9, 2014

(54) TRPM8 RECEPTOR ANTAGONISTS

(75) Inventors: Alessio Moriconi, L'Aquila (IT); Gianluca Bianchini, L'Aquila (IT); Andrea Aramini, L'Aquila (IT); Laura Brandolini, L'Aquila (IT); Chiara Liberati, Milan (IT); Silvia Bovolenta, Milan (IT); Andrea Beccari, L'Aquila (IT); Simone Lorenzi, L'Aquila (IT)

(73) Assignee: Dompe' S.p.A., L'Aquila (AQ) (IT)

( * ) Notice: Subject to any disclaimer, the term of this patent is extended or adjusted under 35 U.S.C. 154(b) by 0 days.

(21) Appl. No.: 13/982,235

(22) PCT Filed: Jan. 27, 2012

(86) PCT No.: PCT/EP2012/051292
§ 371 (c)(1),
(2), (4) Date: Oct. 14, 2013

(87) PCT Pub. No.: WO2012/101244
PCT Pub. Date: Aug. 2, 2012

(65) Prior Publication Data
US 2014/0031398 A1 Jan. 30, 2014

(30) Foreign Application Priority Data
Jan. 28, 2011 (EP) .................................. 11425021

(51) Int. Cl.
| | | |
|---|---|---|
| C07D 207/335 | (2006.01) |
| C07D 213/38 | (2006.01) |
| C07D 307/52 | (2006.01) |
| C07D 333/20 | (2006.01) |
| A61K 31/44 | (2006.01) |
| C07D 213/36 | (2006.01) |
| C07D 207/323 | (2006.01) |
| C07D 307/56 | (2006.01) |
| C07D 333/28 | (2006.01) |

(52) U.S. Cl.
CPC ............ *C07D 213/38* (2013.01); *C07D 333/20* (2013.01); *C07D 213/36* (2013.01); *C07D 307/52* (2013.01); *C07D 207/323* (2013.01); *C07D 307/56* (2013.01); *C07D 207/335* (2013.01); *C07D 333/28* (2013.01)
USPC ........... 514/357; 514/427; 514/438; 514/471; 546/329; 546/334; 548/561; 549/74; 549/75; 549/492; 549/495

(58) Field of Classification Search
None
See application file for complete search history.

(56) References Cited

U.S. PATENT DOCUMENTS
2010/0160289 A1   6/2010   Macielag

FOREIGN PATENT DOCUMENTS

| WO | WO2006040136 A1 | 4/2006 |
|---|---|---|
| WO | WO2007017092 A1 | 2/2007 |
| WO | WO2007017093 A1 | 2/2007 |
| WO | WO2007017094 A1 | 2/2007 |
| WO | WO2007080109 A1 | 7/2007 |
| WO | WO2009012430 A1 | 1/2009 |
| WO | WO2007134107 A3 | 3/2009 |
| WO | WO2010103381 A1 | 9/2010 |
| WO | WO2010125831 A1 | 11/2010 |

OTHER PUBLICATIONS

Behrendt et al., "Characterization of the Mouse Cold-Menthol Receptor TRPM8 and Vanilloid Receptor Type-1 VR1 using a Flourometric Imaging Plate Reader (FLIPR) Assay," British Journal of Pharmacology (Feb. 2004)141(4): 737-745.

(Continued)

*Primary Examiner* — Zinna Northington Davis
(74) *Attorney, Agent, or Firm* — Fish & Richardson P.C.

(57) ABSTRACT

Compounds acting as selective antagonists of Transient Receptor Potential cation channel subfamily M member 8 (hereinafter referred to as TRPM8), having formula:

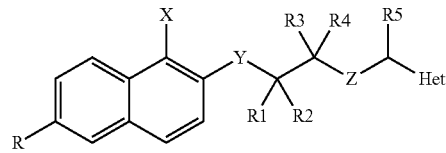

Figure 3:
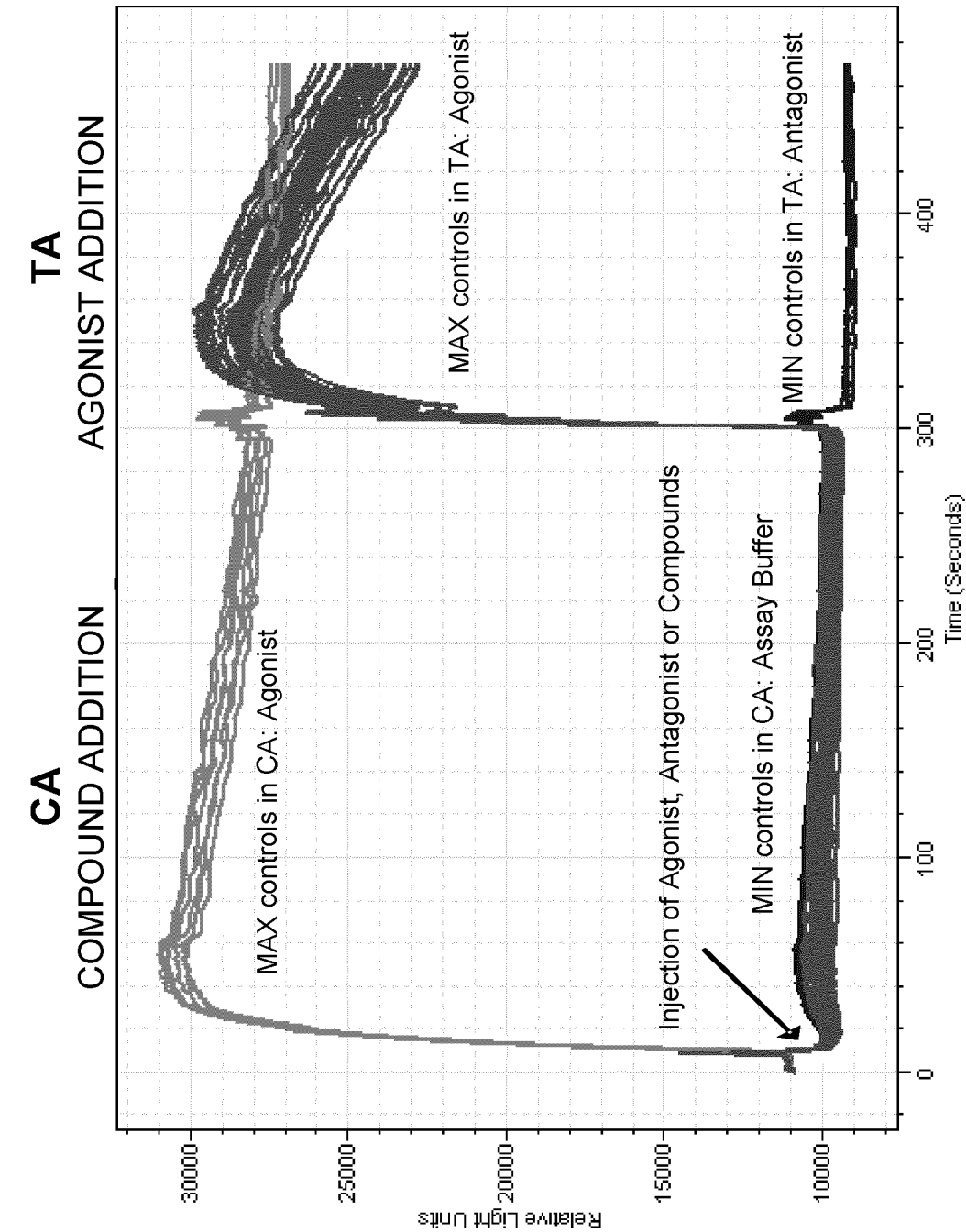

Wherein
R is selected from:
H, Br, CN, $NO_2$, $SO_2NH_2$, $SO_2NHR'$ and $SO_2NR'_2$, where R' is selected from linear or branched $C_1$-$C_4$ alkyl;
X is selected from:
F, Cl, $C_1$-$C_3$ alkyl, $NH_2$ and OH
Y is selected from:
O, $CH_2$, NH and $SO_2$
R1 and R2, independently one from the other, are selected from
H, F and linear or branched $C_1$-$C_4$ alkyl;
R3 and R4, independently one from the other, are selected from
H and linear or branched $C_1$-$C_4$ alkyl;
Z is selected from:
NR6 and $R6R7N^+$, where R6 and R7 independently one from the other, are selected from:
H and linear or branched $C_1$-$C_4$ alkyl R5 is a residue selected from:
H and linear or branched $C_1$-$C_4$ alkyl
Het is a heteroaryl group selected from
a substituted or not substituted pyrrolyl, a substituted or not substituted N-methylpyrrolyl, a substituted or not substituted thiophenyl, a substituted or not substituted furyl and a substituted or not substituted pyridinyl.
Said compounds are useful in the prevention and treatment of pathologies depending on TRPM8 activity such as pain, inflammation, ischaemia, neurodegeneration, stroke, psychiatric disorders, inflammatory conditions and urological disorders.

16 Claims, 3 Drawing Sheets

(56) References Cited

OTHER PUBLICATIONS

EPO Authorized Officer Stewart Bissmire, International Search Report and Written Opinion from corresponding International Application No. PCT/EP2012/051292 mailed Apr. 2, 2013 (12 pages).

Liu and Qin, "TRPM8 in Health and Disease: Cold Sensing and Beyond," Advances in Experimental Medicine and Biology, 704: 185-208 (2011).

W.C. De Groat, "A Neurologic Basis for the Overactive Bladder," Urology (1997) 50, 36-52.

L. De Petrocellis t al., "Regulation of transient receptor potential channels of melastatin type 8 (TRPM8): Effect of cAMP, cannabinoid CBI receptors and endovanilloids," Exp.Cell. Res. (Jan. 2007) 313, 1911-1920.

W. Everaerts et al., "On the Origin of Bladder Sensing: Tr(i)ps in Urology," Neurourology and Urodynamics (2008) 27, 264-73.

S.M. Henshall et al., "Survival Analysis of Genome-Wide Gene Expression Profiles of Prostate Cancers Identifies New Prognostic Targets of Disease Relapse," Cancer Res. (Jul. 2003) 63, 4196-4203.

M. Lazzeri et al., "TRP family proteins in the lower urinary tract: translating basic science into new clinical prospective," Therapeutic Advances in Urology (2009), 1, 33-42.

D. D. McKemy et al., Identification of a cold receptor reveals a general role for TRP channels in thermosensation, Nature (Mar. 2002) 416, 52-58.

G. R. Monteith et al., "Calcium and cancer: targeting Ca2+ transport" Nature Reviews Cancer (Jul. 2007) 7, 519-530.

G. Mukerji G. et al., "Pain during ice water test distinguishes clinical bladder hypersensitivity from overactivity disorders," BMC Urology (Dec. 2006), 6, 31-36.

G. Mukerji et al., "Cool and menthol receptor TRPM8 in human urinary bladder disorders and clinical correlations," BMC Urology (Mar. 2006), 6:6.

B. Nilius et al., "TRP Channels in Disease," Science STKE (Aug. 2005), 295, re8, 9 pp.

B. Nilius et al., "TRP channels in disease," Biochim. Biophys. Acta (2007), 1772, 805-12.

B. Nilius et al., "Gating of TRP channels: a voltage connection?"J. Physiol. (May 2005) 567.1, 35-44.

B. Nilius et al., "Transient Receptor Potential Cation Channels in Disease," Physiol. Rev. (Jan. 2007), 87, 165-217.

C. J. Proudfoot et al., "Analgesia Mediated by the TRPM8 Cold Receptor in Chronic Neuropathic Pain," Curr. Biol. (Aug. 2006), 16, 1591-1605.

A. Gennaro et al., "Part 8: Pharmaceutical Preparations and their Manufacture," Remington's Pharmaceutical Sciences, MACK Publishing, New York, 18th ed., 1990, pp. 1435-1705.

T. Rohacs et al., "PI (4,5)P2 regulates the activation and desensitization of TRPM8 channels through the TRP domain," Nat. Neurosci. (May 2005) 8, 626-634.

L. Tsavaler et al., "Trp-p8, a Novel Prostate-specific Gene, Is Up-Regulated in Prostate Cancer and Other Malignancies and Shares High Homology with Transient Receptor Potential Calcium Channel Proteins," Cancer Res. (May 2001), 61, 3760-3769.

F. Vanden Abeele et al., "Membrane Transport, Structure, and Biogenesis: Ca2+—independent Phospholipase A2—dependent Gating of TRPM8 by Lysophospholipids," J. Biol.Chem. (Nov. 2006) 281, 40174-40182.

U. Wissenbach et al., "TRP channels as potential drug targets," Biol. Cell. (2004), 96, 47-54.

H. Xing et al., "TRPM8 mechanism of autonomic nerve response to cold in respiratory airway," Molecular Pain (Jun. 2008), 4, 22-30.

T. Voets et al., "Sensing with TRP channels," Nat. Chem. Biol. (Jul. 2005), 1, 85-92.

A. M. Peier et al., "A TRP Channel that Senses Cold Stimuli and Menthol," Cell (Mar. 2002) 108, 705-715.

Figure 1

Figure 2

TRPM8 RECEPTOR ANTAGONISTS

CROSS-REFERENCE TO RELATED APPLICATIONS

This application is a National Stage application under 35 U.S.C. §371 of International Application No. PCT/EP2012/051292, having an International Filing Date of Jan. 27, 2012, which claims the benefit of EP Application No. 11425021.0, filed Jan. 28, 2011. The above applications are hereby incorporated by reference in their entirety.

BRIEF DESCRIPTION OF THE INVENTION

The present invention relates to novel naphtyl derivatives that are useful in the treatment or prevention of diseases associated with the activity of the TRPM8 (Transient Receptor Potential cation channel subfamily M member 8), also known as CMR-1 (Cold Menthol Receptor), and in particular in the prevention, reduction of the risk of, amelioration and/or treatment of inflammation, ischaemia, pain neurodegeneration, psychiatric disorders, stroke and urological disorders. The invention further relates to processes for the synthesis of the above compounds and to pharmaceutical compositions containing them.

BACKGROUND OF THE INVENTION

Transient Receptor Potential (TRP) channels are one of the largest group of ion channels that is divided into 6 sub-families (TRPV, TRPM; TRPA, TRPC, TRPP and TRPML). TRP channels are cation-selective channels activated by several physical (temperature, osmolarity and mechanical) and chemical stimuli. TRPM8, which was cloned in 2002, is a non-selective cation channel of the TRP family expressed on a subpopulation of somatic sensory nerves on dorsal root ganglion and trigeminal ganglia that causes sensory nerve excitation. It is activated by mild cold temperatures and synthetic cooling compounds such as menthol, eucalyptol and icilin [McKemy D. D. et al., Nature (2002) 416, 52-58; Peier A. M. et al. Cell (2002) 108, 705-715]. Like several other TRP channels, TRPM8 is also gated by voltage [Nilius B. et al., J. Physiol. (2005) 567, 35-44]. The voltage dependence of TRPM8 is characterized by a strong outward rectification at depolarized transmembrane potential and a rapid and potential-dependent closure at negative membrane potentials. Cooling agents and menthol application shifts the activation curve towards more negative potentials, increasing the possibility for the opening of the channel and boosting inward currents at physiological membrane potentials. Other endogenous factors, such as phospholipase $A_2$ products [Vanden Abeele F. et al., J. Biol. Chem. (2006) 281, 40174-40182], endocannabinoids [De Petrocellis L. et al., Exp. Cell. Res. (2007) 313, 1911-1920] and $PIP_2$ [Rohacs T. et al., Nat. Neurosci. (2005) 8, 626-634] also participate in channel regulation.

There is a lot of direct and indirect evidence of a role of TRPM8 channel activity in diseases such as pain, ischemia and inflammatory disorders. Further, it has been demonstrated that TRP channels transduce reflex signals that are involved in the overactive bladder of patients with damaged or abnormal spinal reflex pathways [De Groat W. C. et al., Urology (1997) 50, 36-52]. TRPM8 is activated by temperatures between 8 and 28° C. and expressed on the primary nociceptive neurons, including bladder urothelium, dorsal root ganglia, A-delta and C-fibers. The intravesical ice water or menthol also induce C-fiber mediated spinal micturition reflex in patients with urgency and urinary incontinence [Everaerts W. et al., Neurol. Urodyn. (2008) 27, 264-73]. Furthermore, TRPM8 is known to regulate $Ca^{2+}$ concentration influxes in response to cold temperature or pharmacological stimuli. Finally, in a recent paper, the potential role of TRPM8 in cold-induced asthma and in asthma exacerbation has been proposed, suggesting TRPM8 also a relevant target for the management of these pathologies [Xing H. et al., Molecular Pain (2008), 4, 22-30], even a clinical validation of the target is not so far available.

Cold intolerance induced by chemical or thermal cooling closely parallels symptoms seen in a wide range of clinical disorders and thus provide a strong rationale for the investigation and development of novel TRPM8 inhibitors as novel antihyperalgesic or antiallodynic agents. The expression of the channel in brain, lung, bladder, gastrointestinal tract, blood vessels, prostate and immune cells provide further possibility for therapeutic modulation in a wide range of pathologies. The disorders or diseases that have been proven to be affected by the modulation of TRPM8 are chronic pain, neuropathic pain including cold allodynia and diabetic neuropathy, postoperative pain, osteoarthritic pain, rheumatoid arthritic pain, cancer pain, neuralgia, neuropathies, algesia, nerve injury, migraine, headaches, ischaemia, neurodegeneration, fibromyalgia, stroke, psychiatric disorders, including anxiety and depression, and inflammatory conditions such as itch, irritable bowel syndrome, or respiratory diseases such as asthma, COPD, and pulmonary hypertension, urological disorders such as painful bladder syndrome, interstitial cystitis, detrusor overactivity (overactive bladder), urinary incontinence, neurogenic detrusor overactivity (detrusor hyperflexia), idiopathic detrusor overactivity (detrusor instability), benign prostatic hyperplasia, lower urinary tract disorders and lower urinary tract symptoms [Nilius B. et al. Science STKE (2005), 295, re8; Voets T. et al., Nat. Chem. Biol. (2005), 1, 85-92; Mukerji G. et al., Urology (2006), 6, 31-36; Lazzeri M. et al., Ther. Adv. Urol. (2009), 1, 33-42; Nilius B. et al., Biochim. Biophys. Acta (2007), 1772, 805-12; Wissenbach U. et al., Biol. Cell. (2004), 96, 47-54; Nilius B. et al., Physiol. Rev. (2007), 87, 165-217; Proudfoot C. J. et al., Curr. Biol. (2006), 16, 1591-1605].

Along the last few years, several classes of non peptide TRPM8 antagonists have been disclosed. WO 2006/040136, WO 2007/017092, WO 2007/017093, WO 2007/017094, and WO 2007/080109 describe benzyloxy derivatives as TRPM8 antagonists for the treatment of urological disorders; WO 2007/134107 describes phosphorous-bearing compounds as TRPM8 antagonists for the treatment of TRPM8-related disorders; WO 2009/012430 describes sulfonamides for the treatment of diseases associated with TRPM8; WO 2010/103381 describes the use of spirocyclic piperidine derivatives as to TRPM8 modulators in prevention or treatment of TRPM8-related disorders or diseases; and, WO 2010/125831 describes sulfamoyl benzoic acid derivatives as modulators of the TRPM8 receptor and their use in the treatment of inflammatory, pain and urological disorders.

However, the TRPM8 antagonists under active development for selected indications suffer from drawbacks such as low selectivity, which results in side effects due to interference with other channel systems and an unfavourable PK/ADMET profile, which could impair their further development.

A therapeutic area in which there is a particularly high need for the development of further antagonists of TRPM8 is that of urological-related disorders. In fact, the drugs and medications that are available for the treatment of urinary incontinence and disorders are characterized by several side effects. For example, at the moment, the therapy of overactive bladder syndrome is based on drugs affecting peripheral neural control mechanisms or mechanisms acting directly on bladder detrusor smooth muscle contraction, with a wide use of anticholinergic agents. These drugs inhibit parasympathetic nerves exerting a direct spasmolytic effect on the muscle of the bladder. The result of this action is the decrease of intravesicular pressure, an increase in capacity and a reduction in the frequency of bladder contraction. However, the use of anticholinergic agents is associated with serious side effects, such as dry mouth, abnormal visions, constipation and CNS disturbances, that impair the overall patient compliance. The inadequacies of the actual therapies highlight the need for novel, efficacious and safe drugs with fewer side effects.

SUMMARY OF THE INVENTION

The present inventors have now found a novel class of compounds acting as selective antagonists of Transient Receptor Potential cation channel subfamily M member 8 (hereinafter referred to as TRPM8), having formula:

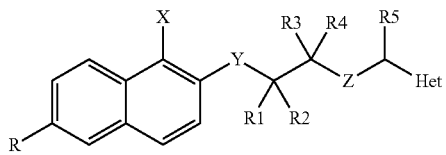

Wherein
R is selected from:
  H, Br, CN, $NO_2$, $SO_2NH_2$, $SO_2NHR'$ and $SO_2N(R')_2$, where R' is selected from linear or branched $C_1$-$C_4$ alkyl;
X is selected from:
  F, Cl, $C_1$-$C_3$ alkyl, $NH_2$ and OH
Y is selected from:
  O, $CH_2$, NH and $SO_2$
R1 and R2, independently one from the other, are selected from
  H, F and linear or branched $C_1$-$C_4$ alkyl;
R3 and R4, independently one from the other, are selected from
  H and linear or branched $C_1$-$C_4$ alkyl;
Z is selected from:
  NR6 and $R6R7N^+$, where R6 and R7 indipendently one from the other, are selected from:
    H and linear or branched $C_1$-$C_4$ alkyl
R5 is a residue selected from:
  H and linear or branched $C_1$-$C_4$ alkyl
Het is a heteroaryl group selected from
  a substituted or not substituted pyrrolyl, a substituted or not substituted N-methylpyrrolyl, a substituted or not substituted thiophenyl, a substituted or not substituted furyl and a substituted or not substituted pyridinyl.

Said compounds are useful in the treatment of pathologies depending on TRPM8 activity.

DETAILED DESCRIPTION OF THE FIGURES

Figure 1:
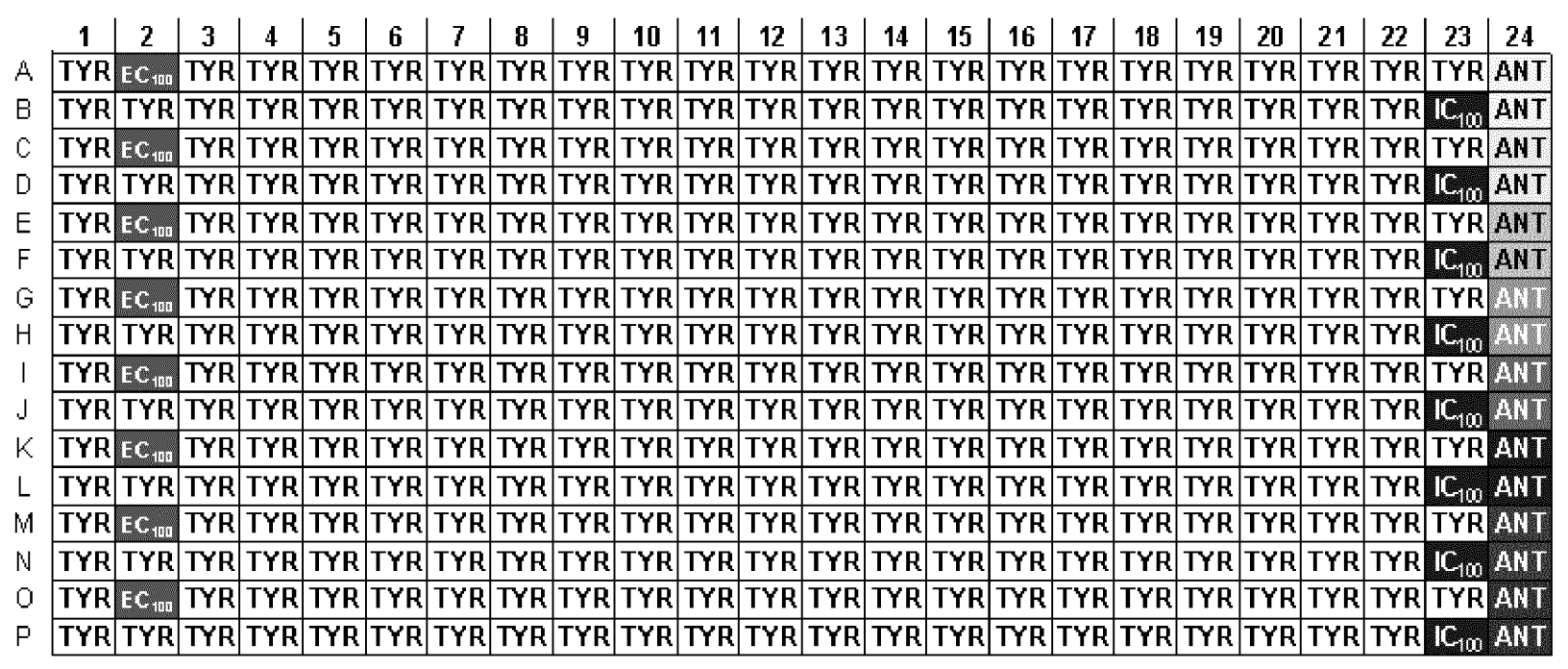

FIG. 1 shows a graphical representation of the 384 wells Compound Dilution Plate Layout used for the biological evaluation of the compounds of the invention as described in Example 62, wherein: in Column 1 wells contain assay buffer plus 0.5% DMSO; in Column 2: wells alternate Max signal control in first injection (Cooling agent 10 at 100 µM, corresponding to $EC_{100}$) and Min signal control in first injection (assay buffer plus 0.5% DMSO final); in columns 3-22: wells contain assay buffer plus 0.5% DMSO final and to each of these wells a compound to be tested is added, at 3× concentrations; in Column 23: wells alternate Max signal control in second injection (Assay Buffer) and Min signal control in second injection (Capsazepine at 50 mm, corresponding to $IC_{100}$); in Column 24: wells contain Capsazepine at 8 different concentrations in duplicate as reported in Example 62.

Figure 2:
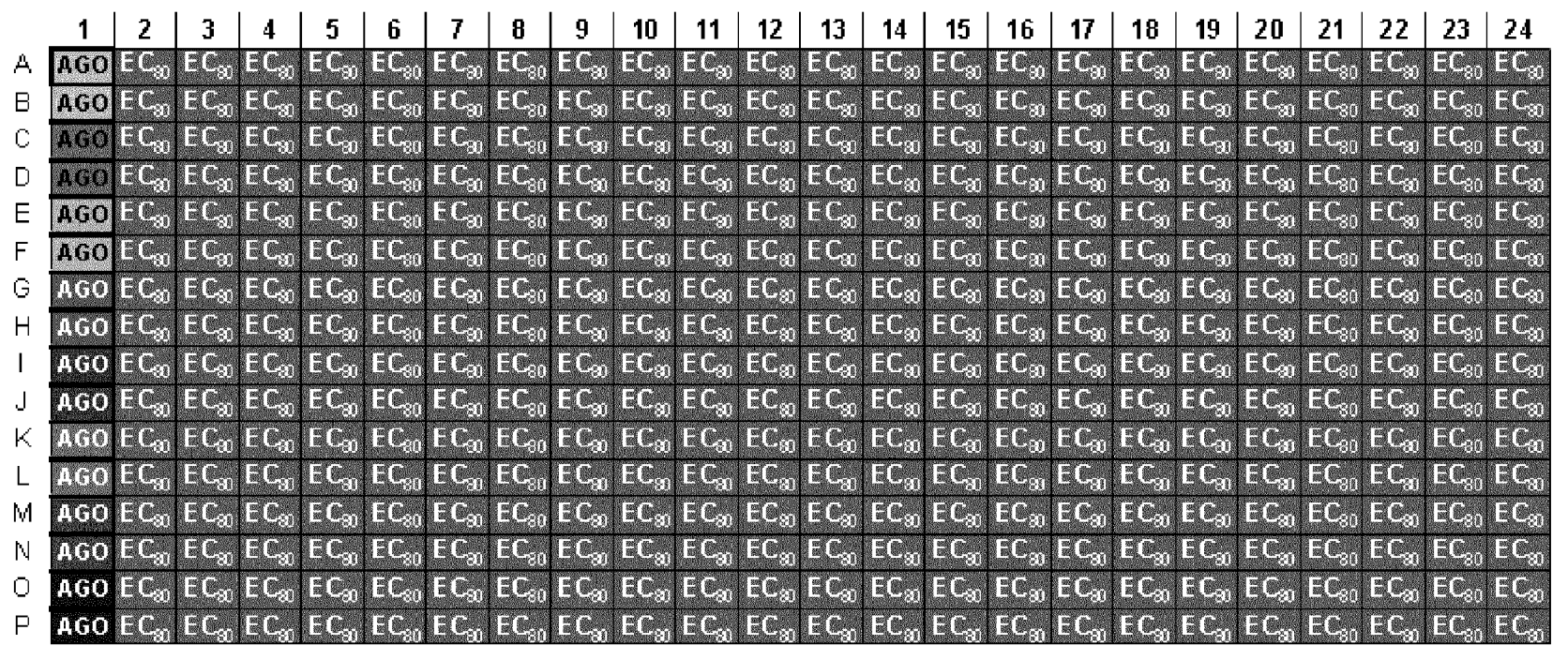

FIG. 2 shows a graphical representation of the 384 wells Activator Plate Layout used for the biological evaluation of the compounds of the invention as described in Example 62. wherein in Column 1 wells contain Cooling Agent 10 at 8 concentrations dose-response in duplicate at different concentrations as reported in Example 62; in Columns 2-24 wells contain Cooling Agent 10 at at $EC_{80}$ (3× concentrations, the highest being 20 µM final).

FIG. 3 shows a graph with a typical kinetic response obtained in the test described in Example 62 for the compounds of Table 1. Signal expressed as Relative Light Units (y-axis), is reported vs time (sec. x-axis) following the injection of a definite amount of control/the test compounds. CA refers to the phase of Compound Addition, while TA to the Target Activation Phase perfomed in presence of the agonist, to increase the MAX Signal control, followed by the injection of a reference inhibitor for the complete abolition of the signal and the registration of the MIN Signal control.

DETAILED DESCRIPTION OF THE INVENTION

A first object of the present invention are compounds of formula (I):

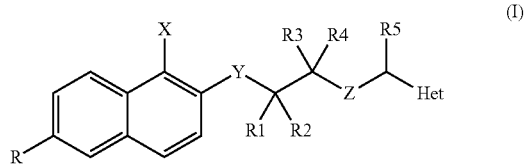

and pharmaceutically acceptable salts thereof,
wherein
R is selected from:
  H, Br, CN, $NO_2$, $SO_2NH_2$, $SO_2NHR'$ and $SO_2N(R')_2$, where R' is selected from linear or branched $C_1$-$C_4$ alkyl;
X is selected from:
  F, Cl, $C_1$-$C_3$ alkyl, $NH_2$ and OH
Y is selected from:
  —O—, $CH_2$, NH and $SO_2$
R1 and R2, independently one from the other, are selected from
  H, F and linear or branched $C_1$-$C_4$ alkyl;
R3 and R4, independently one from the other, are selected from
  H and linear or branched $C_1$-$C_4$ alkyl;
Z is selected from:
  NR6 and $R6R7N^+$, where R6 and R7 indipendently one from the other, are selected from:
    H and linear or branched $C_1$-$C_4$ alkyl
R5 is a residue selected from:
  H and linear or branched $C_1$-$C_4$ alkyl
Het is a heteroaryl group selected from
a substituted or not substituted pyrrolyl, a substituted or not substituted N-methylpyrrolyl, a substituted or not substituted thiophenyl, a substituted or not substituted furyl and a substituted or not substituted pyridinyl, and preferably it is a a substituted or not substituted pyrrol-2-yl, a substituted or not substituted N-methylpyrrol-2-yl, a substituted or not substituted thiophen-2-yl, a substituted or not substituted fur-2-yl, a substituted or not substituted pyridin-2-yl.

According to preferred embodiments of the invention, also in combination one with the other, in the above compounds, independently one from the other:

R is preferably selected from H, Br and CN, and even more preferably from H and CN;

X is preferably selected from F, $C_1$ and $C_1$-$C_3$ alkyl, more preferably from F, $C_1$ and $C_2H_5$, even more preferably from F and Cl;

Y is preferably selected from —O—, $CH_2$, NH and $SO_2$, and, more preferably, from $CH_2$, O and $SO_2$, R1 and R2, independently one from the other, are preferably selected from H, F and $CH_3$, more preferably from H and $CH_3$;

R3 and R4, independently one from the other, are preferably selected from H and $CH_3$;

Z is preferably selected from NR6 and R6R7N$^+$ where R6 and R7, independently one from the other, are selected from H and CH3; more preferably it is NH, R5 is preferably selected from H and $CH_3$ and, more preferably it is H;

According to a further preferred embodiment of the invention, also in combination with all the above embodiments, when Het is a substituted pyrrolyl, a substituted N-methylpyrrolyl, a substituted thiophenyl or a substituted furyl, it is preferably substituted with one or more substituents selected from F, Cl, $CH_3$ $NH_2$ and OH, and more preferably from F, $C_1$ and $CH_3$, even more preferably from $C_1$ and $CH_3$. Preferably, said substituent is in position 5.

Preferred compounds of formula (I) according to the present invention are those listed in Table I, and in details:

2-[(1-chloronaphthalen-2-yl)oxy]-N-(furan-2-ylmethyl) ethanaminium chloride (1)

2-[(1-chloronaphthalen-2-yl)oxy]-N-[(5-methylfuran-2-yl) methyl]ethanaminium chloride (2)

N-[(5-chlorofuran-2-yl)methyl]-2-[(1-chloronaphthalen-2-yl)oxy]ethanaminium (3)

2-[(1-chloronaphthalen-2-yl)oxy]-N-[(5-chlorothiophen-2-yl)methyl]ethanaminium (4)

2-[(1-chloronaphthalen-2-yl)oxy]-N-(thiophen-2-ylmethyl) ethanaminium (5)

2-[(1-chloronaphthalen-2-yl)oxy]-N-(pyridin-2-ylmethyl) ethanaminium (6)

2-[(1-chloronaphthalen-2-yl)oxy]-N-[(1-methyl-1H-pyrrol-2-yl)methyl]ethanaminium (7)

1-[(1-chloronaphthalen-2-yl)oxy]-N-(furan-2-ylmethyl)-2-methylpropan-2-amine (8)

1-[(1-chloronaphthalen-2-yl)oxy]-2-methyl-N-[(5-methylfuran-2-yl)methyl]propan-2-amine (9)

N-[(5-chlorofuran-2-yl)methyl]-1-[(1-chloronaphthalen-2-yl)oxy]-2-methyl propan-2-amine (10)

1-[(1-chloronaphthalen-2-yl)oxy]-N-[(5-chlorothiophen-2-yl)methyl]-2-methyl propan-2-amine (11)

1-[(1-chloronaphthalen-2-yl)oxy]-2-methyl-N-(thiophen-2-ylmethyl)propan-2-amin (12)

1-[(1-chloronaphthalen-2-yl)oxy]-2-methyl-N-(pyridin-2-ylmethyl)propan-2-amine (13)

1-[(1-chloronaphthalen-2-yl)oxy]-2-methyl-N-[(1-methyl-1H-pyrrol-2-yl)methyl]propan-2-amine (14)

2-[(1-chloronaphthalen-2-yl)oxy]-N-(furan-2-ylmethyl)propan-1-amine (15)

2-[(1-chloronaphthalen-2-yl)oxy]-N-[(5-methylfuran-2-yl) methyl]propan-1-amine (16)

N-[(5-chlorofuran-2-yl)methyl]-2-[(1-chloronaphthalen-2-yl)oxy]propan-1-amine (17)

2-[(1-chloronaphthalen-2-yl)oxy]-N-[(5-chlorothiophen-2-yl)methyl]propan-1-amine (18)

2-[(1-chloronaphthalen-2-yl)oxy]-N-(thiophen-2-ylmethyl) propan-1-amine (19)

1-[(1-chloronaphthalen-2-yl)oxy]-N-(furan-2-ylmethyl)propan-2-amine (20)

1-[(1-chloronaphthalen-2-yl)oxy]-N-[(5-methylfuran-2-yl) methyl]propan-2-amine (21)

N-[(5-chlorofuran-2-yl)methyl]-1-[(1-chloronaphthalen-2-yl)oxy]propan-2-amine (22)

1-[(1-chloronaphthalen-2-yl)oxy]-N-[(5-chlorothiophen-2-yl)methyl]propan-2-amine (23)

1-[(1-chloronaphthalen-2-yl)oxy]-N-(thiophen-2-ylmethyl) propan-2-amine (24)

2-[(1-chloronaphthalen-2-yl)sulfonyl]-N-(furan-2-ylmethyl)ethanamine (25)

2-[(1-chloronaphthalen-2-yl)sulfonyl]-N-[(5-methylfuran-2-yl)methyl]ethanamine (26)

N-[(5-chlorofuran-2-yl)methyl]-2-[(1-chloronaphthalen-2-yl)sulfonyl]ethanamine (27)

2-[(1-chloronaphthalen-2-yl)sulfonyl]-N-[(5-chlorothiophen-2-yl)methyl]ethanamine (28)

2-[(1-chloronaphthalen-2-yl)sulfonyl]-N-(thiophen-2-ylmethyl)ethanamine (29)

2-[(1-chloronaphthalen-2-yl)sulfonyl]-N-(pyridin-2-ylmethyl)ethanamine (30)

2-[(1-chloronaphthalen-2-yl)sulfonyl]-N-[(1-methyl-1H-pyrrol-2-yl)methyl]ethanamine (31)

3-(1-chloronaphthalen-2-yl)-N-(furan-2-ylmethyl)propan-1-amine (32)

3-(1-chloronaphthalen-2-yl)-N-[(5-methylfuran-2-yl)methyl]propan-1-amine (33)

N-[(5-chlorofuran-2-yl)methyl]-3-(1-chloronaphthalen-2-yl)propan-1-amine (34)

3-(1-chloronaphthalen-2-yl)-N-[(5-chlorothiophen-2-yl)methyl]propan-1-amine (35)

3-(1-chloronaphthalen-2-yl)-N-(thiophen-2-ylmethyl)propan-1-amine (36)

3-(1-chloronaphthalen-2-yl)-N-(pyridin-2-ylmethyl)propan-1-amine (37)

2-[(1-chloronaphthalen-2-yl)oxy]-N-(furan-2-ylmethyl)-N-methylethanamine (38)

2-[(1-chloronaphthalen-2-yl)oxy]-N-(furan-2-ylmethyl)-N,N-dimethylethanaminium iodide (39)

N-{2-[(1-chloronaphthalen-2-yl)oxy]ethyl}-1-(5-methylfuran-2-yl)ethanamine (40)

N-(1-chloronaphthalen-2-yl)-N'-(furan-2-ylmethyl)ethane-1,2-diamine (41)

N-(1-chloronaphthalen-2-yl)-N'-[(5-methylfuran-2-yl)methyl]ethane-1,2-diamine (42)

N-[(5-chlorofuran-2-yl)methyl]-N'-(1-chloronaphthalen-2-yl)ethane-1,2-diamine (43)

N-(1-chloronaphthalen-2-yl)-N'-[(5-chlorothiophen-2-yl) methyl]ethane-1,2-diamine (44)

N-(1-chloronaphthalen-2-yl)-N'-(thiophen-2-ylmethyl) ethane-1,2-diamine (45)

N-(1-chloronaphthalen-2-yl)-N'-(pyridin-2-ylmethyl) ethane-1,2-diamine (46)

N-(1-chloronaphthalen-2-yl)-N'-[(1-methyl-1H-pyrrol-2-yl) methyl]ethane-1,2-diamine (47)

2-[(1-fluoronaphthalen-2-yl)oxy]-N-(furan-2-ylmethyl) ethanamine (48)

2-[(1-fluoronaphthalen-2-yl)oxy]-N-[(5-methylfuran-2-yl) methyl]ethanamine (49)

N-[(5-chlorofuran-2-yl)methyl]-2-[(1-fluoronaphthalen-2-yl)oxy]ethanamine (50)
N-[(5-chlorothiophen-2-yl)methyl]-2-[(1-fluoronaphthalen-2-yl)oxy]ethanamine (51)
2-[(1-fluoronaphthalen-2-yl)oxy]-N-(thiophen-2-ylmethyl) ethanamine (52)
2-[(1-fluoronaphthalen-2-yl)oxy]-N-(pyridin-2-ylmethyl) ethanamine (53)
2-[(1-fluoronaphthalen-2-yl)oxy]-N-[(1-methyl-1H-pyrrol-2-yl)methyl]ethanamine (54)
5-chloro-6-{2-[(pyridin-2-ylmethyl)amino]ethoxy}naphthalene-2-carbonitrile (55)
5-chloro-6-{2-[(furan-2-ylmethyl)amino]ethoxy}naphthalene-2-carbonitrile (56)
5-chloro-6-(2-{[(5-methylfuran-2-yl)methyl]amino}ethoxy)naphthalene-2-carbonitrile (57)
5-chloro-6-(2-{[(5-chlorofuran-2-yl)methyl]amino}ethoxy)naphthalene-2-carbonitrile (58)
5-chloro-6-(2-{[(5-chlorothiophen-2-yl)methyl]amino}ethoxy)naphthalene-2-carbonitrile (59)
5-chloro-6-{2-[(thiophen-2-ylmethyl)amino]ethoxy}naphthalene-2-carbonitrile (60)
2-[(1-ethylnaphthalen-2-yl)oxy]-N-(furan-2-ylmethyl)ethanamine (61)
2,2-difluoro-2-[(1-fluoronaphthalen-2-yl)oxy]-N-(furan-2-ylmethyl)ethanamine (62)
2-[(6-bromo-1-fluoronaphthalen-2-yl)oxy]-N-(furan-2-ylmethyl)ethanamine (63)

Particularly preferred compounds of formula (I), according to the present invention, are:
2-[(1-chloronaphthalen-2-yl)oxy]-N-(furan-2-ylmethyl)ethanaminium chloride (1)
2-[(1-chloronaphthalen-2-yl)oxy]-N-(thiophen-2-ylmethyl)ethanaminium (5)
2-[(1-chloronaphthalen-2-yl)oxy]-N-(pyridin-2-ylmethyl)ethanaminium (6)
1-[(1-chloronaphthalen-2-yl)oxy]-N-(furan-2-ylmethyl)-2-methylpropan-2-amine (8)
1-[(1-chloronaphthalen-2-yl)oxy]-2-methyl-N-(pyridin-2-ylmethyl)propan-2-amine (13)
1-[(1-chloronaphthalen-2-yl)oxy]-2-methyl-N-[(1-methyl-1H-pyrrol-2-yl)methyl]propan-2-amine (14)
2-[(1-chloronaphthalen-2-yl)sulfonyl]-N-(furan-2-ylmethyl)ethanamine (25)
3-(1-chloronaphthalen-2-yl)-N-(furan-2-ylmethyl)propan-1-amine (32)
3-(1-chloronaphthalen-2-yl)-N-[(5-methylfuran-2-yl)methyl]propan-1-amine (33)
N-[(5-chlorofuran-2-yl)methyl]-3-(1-chloronaphthalen-2-yl)propan-1-amine (34)
3-(1-chloronaphthalen-2-yl)-N-[(5-chlorothiophen-2-yl)methyl]propan-1-amine (35)
2-[(1-fluoronaphthalen-2-yl)oxy]-N-(furan-2-ylmethyl) ethanamine (48)
2-[(1-fluoronaphthalen-2-yl)oxy]-N-(thiophen-2-ylmethyl) ethanamine (52)
2-[(1-fluoronaphthalen-2-yl)oxy]-N-(pyridin-2-ylmethyl) ethanamine (53)
5-chloro-6-{2-[(pyridin-2-ylmethyl)amino]ethoxy}naphthalene-2-carbonitrile (55)
5-chloro-6-{2-[(thiophen-2-ylmethyl)amino]ethoxy}naphthalene-2-carbonitrile (60)

The most preferred compound of the invention is compound 1: [2-[(1-chloronaphthalen-2-yl)oxy]-N-(furan-2-ylmethyl)ethanaminium chloride].

As it will be described in details in the experimental section, the present inventors have found that the above described compounds of the invention are potent antagonists of the activity of TRPM8.

As it will be described in more details hereinbelow, all of the above listed compounds have shown antagonist activity in a high-throughput screening (HTS) of the cellular-based assay for the human TRPM8.

Thus, a second object of the present invention, are the above described compounds of formula (I) for use as antagonists of TRPM8, preferably of human TRPM8.

The activity of one of said compounds has been also confirmed in vivo in an isovolumetric bladder model, an animal model for the evaluation of drugs active on pain induced by contractions of bladder.

Furthermore, as it will be described in the experimental section, the compounds of the invention, compared to those of the prior art, have shown a high selectivity for TRPM8 and thus do not show side effects due to interference with other channel systems observed with other TRPM8 compounds of the prior art.

Accordingly, a third object of the present invention are the above compounds for use as medicaments.

A fourth object of the present invention are the above compounds for use in the prevention, reduction of the risk of, amelioration and/or treatment of a disease associated with activity of TRPM8.

According to the present invention, preferred diseases that are associated to the activation of TRPM8 are pain, ischaemia, neurodegeneration, stroke, psychiatric disorders and inflammatory conditions, urological disorders, preferably in pain, and urological disorders.

Preferably, the compounds of the invention are for use in pain selected from chronic pain, neuropathic pain including cold allodynia and diabetic neuropathy, postoperative pain, osteoarthritic pain, rheumatoid arthritic pain, cancer pain, neuralgia, neuropathies, fibromyalgia, algesia, nerve injury, migraine, headaches; even more preferably the compounds of the invention are for use in chronic and neuropathic pain including cold allodynia.

Preferably, said inflammatory condition is selected from itch, irritable bowel disease and respiratory diseases, the latter being preferably selected from pulmonary hypertension, COPD and asthma.

Preferably, the compounds of the invention are for use in urological disorders selected from painful bladder syndrome, interstitial cystitis, detrusor overactivity (overactive bladder), urinary incontinence, neurogenic detrusor overactivity (detrusor hyperflexia), idiopathic detrusor overactivity (detrusor instability), benign prostatic hyperplasia, lower urinary tract disorders and lower urinary tract symptoms.

Preferably, the compounds of the invention are for use in psychiatric disorders selected from anxiety and depression.

A fifth object of the present invention are pharmaceutical compositions comprising the at least one of the above said compounds of formula I in combination with pharmaceutically acceptable excipients and/or diluents.

According to a preferred embodiment said pharmaceutical composition is for the prevention, reduction of the risk of, amelioration and/or treatment of a disease associated with activity of TRPM8.

According to an embodiment, said pharmaceutical composition contains at least one of the above compounds of formula I as the sole active principle(s). According to an alternative embodiment, said pharmaceutical composition contains at least one of the above compounds of formula I in association with at least one other active principle.

The compounds of the invention of formula (I) are conveniently formulated in pharmaceutical compositions using conventional techniques and excipients such as those described in "Remington's Pharmaceutical Sciences Handbook" MACK Publishing, New York, 18th ed., 1990.

The compounds of the invention can be administered by intravesical instillation, by intravenous injection, as a bolus, in dermatological preparations (creams, lotions, sprays and ointments), by inhalation as well as orally in the form of capsules, tablets, syrup, controlled-release formulations and the like.

According to a preferred embodiment, also in combination with the preceding embodiments, the pharmaceutical formulations of the invention may be for intravescical, intravenous, topical and oral administration.

A sixth object of the present invention is a therapeutic method for the prevention, reduction of the risk of, amelioration and/or treatment of said diseases associated with activity of TRPM8 comprising the administration of the above compound of Formula I in a subject in need thereof.

The compounds of the invention can be administered as the sole active principles or in combination with other therapeutically active compounds.

The average daily dose depends on several factors such as the severity of the disease, the condition, age, sex and weight of the patient. The dose will vary generally from 1 to 1500 mg of compounds of formula (I) per day, optionally divided in multiple administrations.

As it will be shown in the experimental section, the compounds of the invention have a better pharmacokinetic profile compared with other TRPM8 antagonists of the prior art. The compounds of the present invention are preferably prepared with a process comprising reacting the aminic intermediate 1 (A):

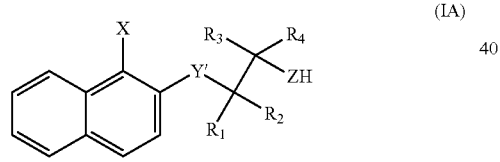

(IA)

wherein X, R1, R2, R3, R4 and Z have the same meanings as those of formula (I) and Y'=O, CH$_2$, NH and S, with R$_5$CO-Het, wherein Het and R$_5$ have the same meanings as those of formula (I), and subsequently adding to the reaction mixture a mild reducing agent, preferably sodium boronhydride, thereby obtaining the compound (IB):

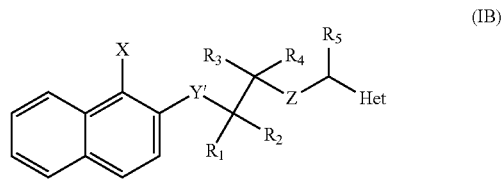

(IB)

which coincides with the final compound of formula (I) in case Y'=O, CH$_2$, NH, or in the case Y'=S this process further contemplates a final oxidation, preferably with m-CPBA (meta-chloroperbenzoic acid) for obtaining the compound of formula (I) having Y=SO$_2$.

The intermediate of formula (IA) is generally prepared with synthetic processes already described in the art.

For example the intermediates (IA) having respectively:
Y'=O are prepared as disclosed in example 1 and in example 9 and in example 49;
Y'=S are prepared as disclosed in example 27,
Y'=CH$_2$ are prepared as dioscolosed in Example 33,
Y'=NH$_2$ are preparedas described in example 41

The present invention shall be illustrated by means of the following examples which are not construed to be viewed as limiting the scope of the invention.

EXAMPLES

Synthesis of Preferred Compounds

The compounds listed in Table I have been synthesized following the procedures described in the following examples.

Materials and Methods $^1$H-NMR spectra were recorded on a Bruker Avance3 400. LC-MS spectra were recorded on a Surveyor (THERMO FINNIGAN) apparatus coupled with a LCQ DECA XP-PLUS (THERMO FINNIGAN) apparatus and equipped with a C18 Phenomenex Gemini column. The eluent mixture consisted of buffer 10 mM pH 4.2 HCOO$^-$NH4$^+$/HCOOH and CH$_3$CN used according the gradient from 90:10 to 10:90 at a flow rate of 0.100 mL/min. GC-MS spectra were recorder on a Trace GC (THERMO FINNIGAN) apparatus coupled with a Trace DSQ Mass spectrometer (THERMO FINNIGAN). All microwave irradiation experiments were carried out using Biotage Initiator 2.5.

Example 1

Synthesis of 2-[(1-chloronaphthalen-2-yl)oxy]-N-(furan-2-ylmethyl)ethanaminiumchloride (1)

Preparation of Intermediates

Tert-butyl (2-bromoethyl)carbamate

To a flask containing 3 g (14.64 mmol) of 2-bromoethanamine dissolved in 40 mL of 1/1 mixture of dichloromethane and water, 3.2 g (14.64 mmol) of di-tert-butyl dicarbonate (BOC$_2$O) and 1.2 g of NaHCO$_3$ were added under stirring. The reaction mixture was allowed to stir at room temperature for 18 h. The phases were separated and the organic layers were dried over Na$_2$SO$_4$. Evaporation of the solvent afforded tert-butyl (2-bromoethyl)carbamate (82% yield) as pale oil which was used without further purification.

$^1$H-NMR (CDCl$_3$) δ: 5.20-4.80 (1H, brs), 3.62-3.34 (4H, m), 1.47 (9H, s).

1-chloronaphthalen-2-ol

To a cooled (0-5° C.) solution of N-chlorosuccinimide (1.4 g, 10.4 mmol) in 100 mL of CH$_2$Cl$_2$, ZrCl$_4$ (0.122 g, 5% mol) was added followed by 1.5 g (10.4 mmol) of naphthalen-2-ol. The mixture was stirred for 18 h at room temperature until the complete disappearance of the starting material as judged by TLC and GC analysis. The mixture was quenched with saturated NH$_4$Cl aqueous solution (30 mL) and transferred to a separatory funnel. The two phases were separated and the organic one was washed with water (3×10 mL), dried over Na$_2$SO$_4$ and evaporated under vacuum to give yellow oil. The crude was purified by flash cromatography (petroleum ether/ethyl acetate 85:15) to afford 1-chloronaphtalen-2-ol (1.4 gr, 78% yield), as white solid.

$^1$H-NMR (CDCl$_3$) δ: 8.08 (1H, ddd, J=0.76 Hz, J=1.88 Hz, J=8.50 Hz), 7.80 (1H, ddd, J=0.76 Hz, J=1.2 Hz, J=8.24 Hz), 7.72 (1H, d, 8.88 Hz), 7.6 (1H, ddd, J=1.2 Hz, J=6.88 Hz, J=8.50 Hz), 7.41 (1H, ddd, J=1.88 Hz, J=6.88 Hz, J=8.24 Hz), 7.28 (1H, d, 8.88 Hz);

GC-MS: m/z 178.

tert-butyl {2-[(1-chloronaphthalen-2-yl)oxy]ethyl}carbamate

To a solution of 1-chloronaphthalen-2-ol (1.68 mmol) and K$_2$CO$_3$ (3.36 mmol) in acetone was added tert-butyl (2-bromoethyl)carbamate (1.85 mmol). The resulting mixture was heated at reflux overnight. After TLC control (n-hexane/ethyl acetate 7:3) showed the disappearance of 1-chloronaphthalen-2-ol, solvent was evaporated in vacuo and the residue was dissolved in 15 mL of ethyl acetate and washed with water (3×5 mL), brine (10 mL) and dried over Na$_2$SO$_4$. The evaporation of solvent afforded tert-butyl {2-[(1-chloronaphthalen-2-yl)oxy]ethyl}carbamate as a grey solid (77% yield) which was used without further purification.

$^1$H-NMR (CDCl$_3$) δ: 8.30 (1H, ddd, J=0.76 Hz, J=1.88 Hz, J=8.50 Hz), 7.88 (1H, ddd, J=0.76 Hz, J=1.2 Hz, J=8.24 Hz), 7.82 (1H, d, 8.88 Hz), 7.65 (1H, ddd, J=1.2 Hz, J=6.88 Hz, J=8.50 Hz), 7.55 (1H, ddd, J=1.88 Hz, J=6.88 Hz, J=8.2 Hz), 7.38 (1H, d, 8.88 Hz), 3.61-3.35 (4H, m), 1.48 (9H, s)

HPLC-MS (ESI+): m/z=322.7 [M+H$^+$]

2-[(1-chloronaphthalen-2-yl)oxy]ethanaminium chloride

To a cooled (0° C.) single necked flask containing a solution of tert-butyl {2-[(1-chloronaphthalen-2-yl)oxy]ethyl}carbamate in 4 mL of ethyl ether, 5 mL of 4 M HCl solution in dioxane were added. The resulting mixture was stirred at room temperature for 18 h. The reaction mixture was concentrated under reduce pressure to afford 2-[(1-chloronaphthalen-2-yl)oxy]ethanaminium chloride as a white solid (92% yield) which was pure by TLC and NMR analysis.

$^1$H-NMR (DMSO-d6) δ: 8.14 (1H, ddd, J=0.76 Hz, J=1.88 Hz, J=8.50 Hz), 8.09 (3H, brs), 8.03-7.94 (2H, m), 7.66 (1H, ddd, J=1.2 Hz, J=6.88 Hz, J=8.50 Hz), 7.60 (1H, d, 8.88 Hz), 7.51 (1H, ddd, J=1.88 Hz, J=6.88 Hz, J=8.2 Hz), 4.40 (2H, t, J=5.60 Hz) 3.38-3.28 (2H, m); HPLC-MS (ESI+): m/z 222.7 [M+H$^+$]

Synthesis of Compound

2-[(1-chloronaphthalen-2-yl)oxy]-N-(furan-2-ylmethyl)ethanaminium chloride (1)

To a solution of 2-[(1-chloronaphthalen-2-yl)oxy]ethanaminium chloride (100 mg, 0.39 mmol) in 10 mL of MeOH, K$_2$CO$_3$ (65 mg, 0.47 mmol) was added. After 10 min, 48 µL (0.58 mmol) of furan-2-carbaldehyde were added. The resulting solution was stirred for 1 h at room temperature, added with sodium borohydride (15 mg, 0.39 mmol) and the reaction was allowed to stir for further 2 h at room temperature. The solvent was evaporated under vacuum; the mixture was diluted with 10 mL CH$_2$Cl$_2$ and transferred to a separatory funnel. The organic layer was washed with water, dried over anhydrous sodium sulfate, filtered, and concentrated in vacuo. The crude product was purified by flash chromatography on silica gel (CH$_2$Cl$_2$/MeOH 95:5) to afford 2-[(1-chloronaphthalen-2-yl)oxy]-N-(furan-2-ylmethyl)ethanamine as a brown oil (63% yield). The oil was left to stir with a 4M HCl dioxane solution for 1 h. The reaction mixture was concentrated under reduce pressure to afford 2-[(1-chloronaphthalen-2-yl)oxy]-N-(furan-2-ylmethyl)ethanaminium chloride as a white solid.

$^1$H-NMR (CDCl$_3$) δ: 10.25 (2H, brs), 8.20 (1H, ddd, J=0.76 Hz, J=1.88 Hz, J=8.50 Hz), 7.80 (1H, ddd, J=0.76 Hz, J=1.2 Hz, J=8.24 Hz), 7.73 (1H, d, 8.88 Hz), 7.60 (1H, ddd, J=1.2 Hz, J=6.88 Hz, J=8.50 Hz), 7.50 (1H, dd, J=0.75 Hz, J=2.01 Hz) 7.45 (1H, ddd, J=1.88 Hz, J=6.88 Hz, J=8.2 Hz), 7.32 (1H, d, 8.88 Hz), 6.79 (1H, dd, J=0.75 Hz, J=3.30 Hz) 6.41 (1H, dd, J=2.01 Hz, J=3.30 Hz) 4.60 (2H, t, J=5.60 Hz), 4.53 (2H, m), 3.46 (2H, t, J=5.60 Hz); HPLC-MS (ESI+): m/z 302.7 [M+H$^+$].

According to the same experimental procedure the following compounds were synthesized:

Example 2

2-[(1-chloronaphthalen-2-yl)oxy]-N-[(5-methylfuran-2-yl)methyl]ethanaminium chloride (2)

Prepared from 2-[(1-chloronaphthalen-2-yl)oxy]ethanaminium chloride and 5-methylfuran-2-carbaldehyde in 70% yield as a white solid.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.56 (1H, d, J=3.37 Hz) 6.11 (1H, qd, J=0.9 Hz, J=3.37 Hz) 4.60 (2H, t, J=5.60 Hz), 4.44 (2H, s), 3.53 (2H, t, J=5.60 Hz), 2.31 (3H, d, J=0.9 Hz); HPLC-MS (ESI+): m/z 316.8 [M+H$^+$].

Example 3

N-[(5-chlorofuran-2-yl)methyl]-2-[(1-chloronaphthalen-2-yl)oxy]ethanaminium (3)

Prepared from 2-[(1-chloronaphthalen-2-yl)oxy]ethanaminium chloride and 5-chlorofuran-2-carbaldehyde in 72% yield as a white solid.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.76 (1H, d, J=3.55 Hz) 6.39 (1H, d, J=3.35 Hz) 4.54-4.46 (4H, m), 3.58 (2H, t, J=5.60 Hz);

HPLC-MS (ESI+): m/z 337.2 [M+H$^+$].

Example 4

2-[(1-chloronaphthalen-2-yl)oxy]-N-[(5-chlorothiophen-2-yl)methyl]ethanaminium (4)

Prepared from 2-[(1-chloronaphthalen-2-yl)oxy]ethanaminium chloride and 5-chlorothiophene-2-carbaldehyde in 78% yield as a white solid.

$^1$H-NMR (CD$_3$OD) δ: 8.20 (1H, ddd, J=0.76 Hz, J=1.88 Hz, J=8.50 Hz), 7.92-7.85 (2H, m), 7.62 (1H, ddd, J=1.2 Hz, J=6.88 Hz, J=8.50 Hz), 7.52-7.44 (2H, m), 7.20 (1H, d, J=3.80 Hz) 7.02 (1H, d, J=3.80 Hz) 4.61 (2H, s), 4.51 (2H, t, J=5.60 Hz), 3.60 (2H, t, J=5.60 Hz); HPLC-MS (ESI+): m/z 353.3 [M+H$^+$].

Example 5

2-[(1-chloronaphthalen-2-yl)oxy]-N-(thiophen-2-ylmethyl)ethanaminium (5)

Prepared from 2-[(1-chloronaphthalen-2-yl)oxy]ethanaminium chloride and thiophene-2-carbaldehyde in 72% yield as a white solid.

$^1$H-NMR (CD$_3$OD) δ: 8.20 (1H, ddd, J=0.76 Hz, J=1.88 Hz, J=8.50 Hz), 7.92-7.85 (2H, m), 7.65-7.55 (2H, m), 7.52-7.44 (2H, m), 7.40-7.35 (1H, m) 7.14 (1H, dd, J=3.50 Hz, J=5.30 Hz) 4.70 (2H, s), 4.51 (2H, t, J=5.6 Hz), 3.60 (2H, t, J=5.6 Hz);

HPLC-MS (ESI+): m/z 318.8 [M+H$^+$].

Example 6

2-[(1-chloronaphthalen-2-yl)oxy]-N-(pyridin-2-ylmethyl)ethanaminium (6)

Prepared from 2-[(1-chloronaphthalen-2-yl)oxy]ethanaminium chloride and pyridine-2-carbaldehyde in 81% yield as a white solid.

$^1$H-NMR (CD$_3$OD) δ: 8.72 (1H, m), 8.20 (1H, ddd, J=0.76 Hz, J=1.88 Hz, J=8.50 Hz), 8.01 (1H, dd, J=1.70 Hz, J=7.78 Hz), 7.95-7.85 (2H, m), 7.75-7.68 (1H, m), 7.65-7.55 (2H, m), 7.52-7.42 (2H, m) 4.70 (2H, s), 4.58 (2H, t, J=5.60 Hz), 3.71 (2H, t, J=5.60 Hz);

HPLC-MS (ESI+): m/z 313.8 [M+H$^+$].

Example 7

2-[(1-chloronaphthalen-2-yl)oxy]-N-[(1-methyl-1H-pyrrol-2-yl)methyl]ethanaminium (7)

Prepared from 2-[(1-chloronaphthalen-2-yl)oxy]ethanaminium chloride and 1-methyl-1H-pyrrole-2-carbaldehyde in 83% yield as a white solid.

$^1$H-NMR (CD$_3$OD) δ: 8.20 (1H, ddd, J=0.76 Hz, J=1.88 Hz, J=8.50 Hz), 7.93-7.83 (2H, m), 7.61 (1H, ddd, J=1.2 Hz, J=6.88 Hz, J=8.50 Hz), 7.52-7.40 (2H, m), 6.78 (1H, dd, J=1.80 Hz, J=2.60 Hz), 6.40 (1H, dd, J=1.80 Hz, J=3.72 Hz) 6.10 (1H, dd, J=2.60 Hz, J=3.72 Hz) 4.55-4.45 (4H, m), 3.73 (3H, s), 3.61 (2H, t, J=5.60 Hz); HPLC-MS (ESI+): m/z 315.8 [M+H$^+$].

Example 8

N-{2-[(1-chloronaphthalen-2-yl)oxy]ethyl}-1-(5-methylfuran-2-yl)ethanamine (40)

Prepared from 2-[(1-chloronaphthalen-2-yl)oxy]ethanaminium chloride and 1-(5-methylfuran-2-yl)ethanone in 34% yield as a pale yellow oil.

$^1$H-NMR (CD$_3$OD) δ: 8.15 (1H, ddd, J=0.76 Hz, J=1.88 Hz, J=8.50 Hz), 7.86-7.73 (2H, m), 7.56 (1H, ddd, J=1.2 Hz, J=6.88 Hz, J=8.50 Hz), 7.47-7.32 (2H, m), 6.10 (1H, d, J=3.45 Hz), 5.85 (1H, qd, J=1.28 Hz, J=3.45 Hz) 4.25 (2H, t, J=5.30 Hz), 3.91 (1H, q, J=7 Hz), 2.95 (2H, t, J=5.30 Hz), 2.18 (3H, d, J=1.28 Hz), 1.42 (3H, d, J=7 Hz); HPLC-MS (ESI+): m/z 330.7 [M+H$^+$].

Example 9

Synthesis of 1-[(1-chloronaphthalen-2-yl)oxy]-N-(furan-2-ylmethyl)-2-methylpropan-2-amine (8)

Preparation of Intermediates

General Synthesis of Bromoethylamino-N-BOC Derivatives 16.4 mmol of the appropriate ethanolamine was added through a dropping funnel to 7 mL (52 mmoles) of ice-cold 48% aqueous hydrobromic acid. The mixture was then heated at 90° C. for 3 h. The solvent was distilled off under vacuum, the crude product was re-dissolved in 40 mL of dichloromethane and 3.2 g (14.64 mmol) of di-tert-butyl dicarbonate (BOC$_2$O) were added. Finally 1N NaOH solution was added under stirring until pH 10.

The reaction mixture was allowed to stir at room temperature for 18 h. The phases were separated and the organic layers were dried over Na$_2$SO$_4$. Evaporation of the solvent afforded the bromoamines as pale oil which was used without further purification. The following intermediates were prepared:

tert-butyl (2-bromopropyl)carbamate

81% yield; $^1$H-NMR (CD$_3$Cl) δ: 3.92 (1H, m), 3.2 (2H, m), 1.48 (9H, s), 1.36 (3H, d, J=7.08 Hz).

tert-butyl (1-bromopropan-2-yl)carbamate

73% yield; $^1$H-NMR (CD$_3$Cl) δ: 3.96 (2H, m), 3.31 (1H, m), 1.48 (9H, s), 1.30 (3H, d, J=7.08 Hz).

tert-butyl (1-bromo-2-methylpropan-2-yl)carbamate

57% yield; $^1$H-NMR (CD$_3$Cl) δ: 3.80 (2H, s), 1.48 (9H, s), 1.40 (6H, s).

1-[(1-chloronaphthalen-2-yl)oxy]-2-methylpropan-2-amine

To a solution of 1-chloronaphthalen-2-ol (1.5 mmol) and Cs$_2$CO$_3$ (3 mmol) in acetonitrile was added tert-butyl (1-bromo-2-methylpropan-2-yl)carbamate (3 mmol). The resulting mixture was heated at reflux overnight. After TLC control (n-hexane/ethyl acetate 7:3) showed the disappearance of 1-chloronaphthalen-2-ol, solvent was evaporated in vacuo and the residue was dissolved in 15 mL of ethyl acetate and washed with water (3×5 mL), brine (10 mL) and dried over Na$_2$SO$_4$. The evaporation of solvent afforded tert-butyl {1-[(1-chloronaphthalen-2-yl)oxy]-2-methylpropan-2-yl}carbamate as a pale oil (51% yield) which was dissolved in 5 mL of 4 M HCl solution in dioxane. The resulting mixture was stirred at room temperature for 18 h. After HPLC-MS control, the solvent was distilled off and the residue was dissolved in dichloromethane and wash 2 times with NaOH 1N to afford 1-[(1-chloronaphthalen-2-yl)oxy]-2-methylpropan-2-amine as a pale oil.

HPLC-MS (ESI+): m/z 250.7 [M+H$^+$].

Example 10

Following the same procedure described but using different intermediates, the following compounds have been synthesised:

1-[(1-chloronaphthalen-2-yl)oxy]-N-(furan-2-ylmethyl)-2-methylpropan-2-amine (8)

Prepared from 1-[(1-chloronaphthalen-2-yl)oxy]-2-methylpropan-2-amine and furan-2 carbaldehyde in 34% yield as a pale oil.

$^1$H-NMR (CDCl$_3$) δ: 8.20 (1H, ddd, J=0.76 Hz, J=1.88 Hz, J=8.50 Hz), 7.80 (1H, ddd, J=0.76 Hz, J=1.2 Hz, J=8.24 Hz), 7.73 (1H, d, 8.88 Hz), 7.60 (1H, ddd, J=1.2 Hz, J=6.88 Hz, J=8.50 Hz), 7.50 (1H, dd, J=0.75 Hz, J=2.01 Hz) 7.45 (1H, ddd, J=1.88 Hz, J=6.88 Hz, J=8.2 Hz), 7.32 (1H, d, 8.88 Hz), 6.79 (1H, dd, J=0.75 Hz, J=3.30 Hz) 6.41 (1H, dd, J=2.01 Hz, J=3.30 Hz) 4.52 (2H, s), 3.66 (2H, s), 1.10 (6H, s); HPLC-MS (ESI+): m/z 330.8 [M+H$^+$].

Example 11

1-[(1-chloronaphthalen-2-yl)oxy]-2-methyl-N-[(5-methylfuran-2-yl)methyl]propan-2-amine (9)

Prepared from 1-[(1-chloronaphthalen-2-yl)oxy]-2-methylpropan-2-amine and 5-methylfuran-2 carbaldehyde in 41% yield as a yellow oil.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.56 (1H, d, J=3.37 Hz) 6.11 (1H, qd, J=0.9 Hz, J=3.37 Hz), 4.50 (2H, s), 3.66 (2H, s), 2.31 (3H, d, J=0.9 Hz), 1.10 (6H, s); HPLC-MS (ESI+): m/z 344.6 [M+H$^+$].

Example 12

N-[(5-chlorofuran-2-yl)methyl]-1-[(1-chloronaphthalen-2-yl)oxy]-2-methylpropan-2-amine (10)

Prepared from 1-[(1-chloronaphthalen-2-yl)oxy]-2-methylpropan-2-amine and 5-chlorofuran-2 carbaldehyde in 32% yield as a yellow oil.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.76 (1H, d, J=3.55 Hz) 6.39 (1H, d, J=3.35 Hz), 4.55 (2H, s), 3.66 (2H, s), 1.10 (6H, s); HPLC-MS (ESI+): m/z 365.2 [M+H$^+$].

Example 13

1-[(1-chloronaphthalen-2-yl)oxy]-N-[(5-chlorothiophen-2-yl)methyl]-2-methylpropan-2-amine (11)

Prepared from 1-[(1-chloronaphthalen-2-yl)oxy]-2-methylpropan-2-amine and 5-chlorothiophen-2 carbaldehyde in 29% yield as a brown oil.

$^1$H-NMR (CD$_3$OD) δ: 8.20 (1H, ddd, J=0.76 Hz, J=1.88 Hz, J=8.50 Hz), 7.92-7.85 (2H, m), 7.62 (1H, ddd, J=1.2 Hz, J=6.88 Hz, J=8.50 Hz), 7.52-7.44 (2H, m), 7.20 (1H, d, J=3.80 Hz) 7.02 (1H, d, J=3.80 Hz), 4.55 (2H, s), 3.69 (2H, s), 1.10 (6H, s); HPLC-MS (ESI+): m/z 381.3 [M+H$^+$].

Example 14

1-[(1-chloronaphthalen-2-yl)oxy]-2-methyl-N-(thiophen-2-ylmethyl)propan-2-amine (12)

Prepared from 1-[(1-chloronaphthalen-2-yl)oxy]-2-methylpropan-2-amine and thiophen-2 carbaldehyde in 40% yield as a brown oil.

$^1$H-NMR (CD$_3$OD) δ: 8.20 (1H, ddd, J=0.76 Hz, J=1.88 Hz, J=8.50 Hz), 7.92-7.85 (2H, m), 7.65-7.55 (2H, m), 7.52-7.44 (2H, m), 7.40-7.35 (1H, m) 7.14 (1H, dd, J=3.50 Hz, J=5.30 Hz), 4.52 (2H, s), 3.68 (2H, s), 1.10 (6H, s); HPLC-MS (ESI+): m/z 346.9 [M+H$^+$].

Example 15

1-[(1-chloronaphthalen-2-yl)oxy]-2-methyl-N-(pyridin-2-ylmethyl)propan-2-amine (13)

Prepared from 1-[(1-chloronaphthalen-2-yl)oxy]-2-methylpropan-2-amine and pyridine-2 carbaldehyde in 34% yield as a colourless oil.

$^1$H-NMR (CD$_3$OD) δ: 8.72 (1H, m), 8.20 (1H, ddd, J=0.76 Hz, J=1.88 Hz, J=8.50 Hz), 8.01 (1H, dd, J=1.70 Hz, J=7.78 Hz), 7.95-7.85 (2H, m), 7.75-7.68 (1H, m), 7.65-7.55 (2H, m), 7.52-7.42 (2H, m) 4.70 (2H, s), 4.52 (2H, s), 1.10 (6H, s); HPLC-MS (ESI+): m/z 341.7 [M+H$^+$].

Example 16

1-[(1-chloronaphthalen-2-yl)oxy]-2-methyl-N-[(1-methyl-1H-pyrrol-2-yl)methyl]propan-2-amine (14)

Prepared from 1-[(1-chloronaphthalen-2-yl)oxy]-2-methylpropan-2-amine and methyl-1H-pyrrole-2-carbaldehyde in 39% yield as a red oil.

$^1$H-NMR (CD$_3$OD) δ: 8.20 (1H, ddd, J=0.76 Hz, J=1.88 Hz, J=8.50 Hz), 7.93-7.83 (2H, m), 7.61 (1H, ddd, J=1.2 Hz, J=6.88 Hz, J=8.50 Hz), 7.52-7.40 (2H, m), 6.78 (1H, dd, J=1.80 Hz, J=2.60 Hz), 6.40 (1H, dd, J=1.80 Hz, J=3.72 Hz) 6.10 (1H, dd, J=2.60 Hz, J=3.72 Hz) 4.60-4.40 (4H, m), 3.73 (3H, s), 1.10 (6H, s); HPLC-MS (ESI+): m/z 343.9 [M+H$^+$].

Example 17

2-[(1-chloronaphthalen-2-yl)oxy]-N-(furan-2-ylmethyl)propan-1-amine (15)

Prepared from 2-[(1-chloronaphthalen-2-yl)oxy]propan-1-amine and furan-2-carbaldehyde in 56% yield as a red oil.

$^1$H-NMR (Acetone-d6) δ: 8.20 (1H, ddd, J=0.76 Hz, J=1.88 Hz, J=8.50 Hz), 8.00-7.85 (2H, m), 7.60 (1H, ddd, J=1.2 Hz, J=6.88 Hz, J=8.50 Hz), 7.53 (1H, dd, J=0.75 Hz, J=2.01 Hz) 7.48 (1H, ddd, J=1.88 Hz, J=6.88 Hz, J=8.2 Hz), 7.44 (1H, d, 8.88 Hz), 6.34 (1H, dd, J=0.75 Hz, J=3.30 Hz) 6.24 (1H, dd, J=2.01 Hz, J=3.30 Hz) 4.83-4.70 (1H, m), 3.85 (2H, s), 3.04-2.84 (2H, m), 1.40 (3H, d, J=7.08 Hz); HPLC-MS (ESI+) m/z 316.8 [M+H$^+$].

Example 18

2-[(1-chloronaphthalen-2-yl)oxy]-N-[(5-methylfuran-2-yl)methyl]propan-1-amine (16)

Prepared from 2-[(1-chloronaphthalen-2-yl)oxy]propan-1-amine and 5-methylfuran-2-carbaldehyde in 70% yield as a yellow oil.

Example 19

N-[(5-chlorofuran-2-yl)methyl]-2-[(1-chloronaphthalen-2-yl)oxy]propan-1-amine (17)

Prepared from 2-[(1-chloronaphthalen-2-yl)oxy]propan-1-amine and 5-chlorofuran-2-carbaldehyde in 77% yield as a colourless oil.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.76 (1H, d, J=3.55 Hz) 6.39 (1H, d, J=3.35 Hz), 4.83-4.70 (1H, m), 3.85 (2H, s), 3.04-2.84 (2H, m), 1.40 (3H, d, J=7.08 Hz); HPLC-MS (ESI+): m/z 351.1 [M+H$^+$].

Example 20

2-[(1-chloronaphthalen-2-yl)oxy]-N-[(5-chlorothiophen-2-yl)methyl]propan-1-amine (18)

Prepared from 2-[(1-chloronaphthalen-2-yl)oxy]propan-1-amine and 5-chlorothiophen-2-carbaldehyde in 69% yield as a yellow oil.

$^1$H-NMR (CD$_3$OD) δ: 8.24 (1H, ddd, J=0.76 Hz, J=1.88 Hz, J=8.50 Hz), 7.92-7.85 (2H, m), 7.62 (1H, ddd, J=1.2 Hz, J=6.88 Hz, J=8.50 Hz), 7.52-7.44 (2H, m), 7.20 (1H, d, J=3.80 Hz) 7.02 (1H, d, J=3.80 Hz), 4.83-4.70 (1H, m), 3.85 (2H, s), 3.04-2.84 (2H, m), 1.40 (3H, d, J=7.08 Hz); HPLC-MS (ESI+): m/z 367.2 [M+H$^+$].

Example 21

2-[(1-chloronaphthalen-2-yl)oxy]-N-(thiophen-2-ylmethyl)propan-1-amine (19)

Prepared from 2-[(1-chloronaphthalen-2-yl)oxy]propan-1-amine and thiophen-2-carbaldehyde in 81% yield as a pale yellow oil.

$^1$H-NMR (CD$_3$OD) δ: 8.15 (1H, ddd, J=0.76 Hz, J=1.88 Hz, J=8.50 Hz), 7.92-7.85 (2H, m), 7.65-7.55 (2H, m), 7.52-7.44 (2H, m), 7.40-7.35 (1H, m) 7.14 (1H, dd, J=3.50 Hz, J=5.30 Hz) 4.83-4.70 (1H, m), 3.95 (2H, s), 3.04-2.84 (2H, m), 1.40 (3H, d, J=7.08 Hz);
HPLC-MS (ESI+): m/z 332.9 [M+H$^+$].

Example 22

1-[(1-chloronaphthalen-2-yl)oxy]-N-(furan-2-ylmethyl)propan-2-amine (20)

Prepared from 1-[(1-chloronaphthalen-2-yl)oxy]propan-2-amine and furan-2-carbaldehyde in 85% yield as a yellow oil.

$^1$H-NMR (CD$_3$OD) δ: 8.17 (1H, ddd, J=0.76 Hz, J=1.88 Hz, J=8.50 Hz), 8.00-7.85 (2H, m), 7.60 (1H, ddd, J=1.2 Hz, J=6.88 Hz, J=8.50 Hz), 7.53 (1H, dd, J=0.75 Hz, J=2.01 Hz) 7.48 (1H, ddd, J=1.88 Hz, J=6.88 Hz, J=8.2 Hz), 7.44 (1H, d, 8.88 Hz), 6.34 (1H, dd, J=0.75 Hz, J=3.30 Hz) 6.24 (1H, dd, J=2.01 Hz, J=3.30 Hz), 4.32 (2H, m), 4.15 (2H, s), 3.1 (1H, m), 1.25 (3H, d, J=6.95); HPLC-MS (ESI+): m/z 316.8 [M+H$^+$].

Example 23

1-[(1-chloronaphthalen-2-yl)oxy]-N-[(5-methylfuran-2-yl)methyl]propan-2-amine (21)

Prepared from 1-[(1-chloronaphthalen-2-yl)oxy]propan-2-amine and 5-methylfuran-2-carbaldehyde in 69% yield as a pale yellow oil.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.56 (1H, d, J=3.37 Hz) 6.11 (1H, qd, J=0.9 Hz, J=3.37 Hz), 4.32 (2H, m), 4.15 (2H, s), 3.1 (1H, m), 2.31 (3H, d, J=0.9 Hz), 1.25 (3H, d, J=6.95); HPLC-MS (ESI+): m/z 330.8 [M+H$^+$].

Example 24

N-[(5-chlorofuran-2-yl)methyl]-1-[(1-chloronaphthalen-2-yl)oxy]propan-2-amine (22)

Prepared from 1-[(1-chloronaphthalen-2-yl)oxy]propan-2-amine and 5-chlorofuran-2-carbaldehyde in 61% yield as a whitish oil.

$^1$H-NMR (CD$_3$OD) δ: 8.19 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.76 (1H, d, J=3.55 Hz) 6.39 (1H, d, J=3.35 Hz), 4.39 (2H, s), 4.25 (2H, m), 3.1 (1H, m), 1.29 (3H, d, J=6.95); HPLC-MS (ESI+): m/z 351.2 [M+H$^+$].

Example 25

1-[(1-chloronaphthalen-2-yl)oxy]-N-[(5-chlorothiophen-2-yl)methyl]propan-2-amine (23)

Prepared from 1-[(1-chloronaphthalen-2-yl)oxy]propan-2-amine and 5-chlorothiophen-2-carbaldehyde in 61% yield as a slightly white oil.

$^1$H-NMR (CD$_3$OD) δ: 8.20 (1H, ddd, J=0.76 Hz, J=1.88 Hz, J=8.50 Hz), 7.92-7.85 (2H, m), 7.62 (1H, ddd, J=1.2 Hz, J=6.88 Hz, J=8.50 Hz), 7.52-7.44 (2H, m), 7.20 (1H, d, J=3.80 Hz) 7.02 (1H, d, J=3.80 Hz), 4.39 (2H, s), 4.25 (2H, m), 3.1 (1H, m), 1.29 (3H, d, J=6.95); HPLC-MS (ESI+): m/z 367.2 [M+H$^+$].

Example 26

1-[(1-chloronaphthalen-2-yl)oxy]-N-(thiophen-2-ylmethyl)propan-2-amine (24)

Prepared from 1-[(1-chloronaphthalen-2-yl)oxy]propan-2-amine and thiophen-2-carbaldehyde in 62% yield as a pale yellow oil.

$^1$H-NMR (CD$_3$OD) δ: 8.18 (1H, ddd, J=0.76 Hz, J=1.88 Hz, J=8.50 Hz), 7.92-7.85 (2H, m), 7.65-7.55 (2H, m), 7.52-7.44 (2H, m), 7.40-7.35 (1H, m) 7.14 (1H, dd, J=3.50 Hz, J=5.30 Hz), 4.32 (2H, m), 4.15 (2H, s), 3.1 (1H, m), 1.25 (3H, d, J=6.95); HPLC-MS (ESI+): m/z 332.8 [M+H$^+$].

Example 27

Synthesis of 2-[(1-chloronaphthalen-2-yl)sulfonyl]-N-(furan-2-ylmethyl)ethanamine (25)

Preparation of Intermediates

O-1-chloro-2naphthyl-dimethylthiocarbamate

A solution of 1-chloronaphthalen-2-ol (1.68 mmol, 300 mg) in 10 mL of acetone containing (8.40 mmol, 1.16 g) of potassium carbonate was stirred at room temperature for 30 minutes than dimethylthiocarbamoyl chloride (3.36 mmol, 415 mg) was added. The reaction was refluxed for 4 hours. After total disappearance of starting material (monitored by TLC), the solvent was evaporated under reduced pressure, the residue was treated with dichloromethane and washed with water. The organic layer was dried over anhydrous sodium sulfate. The crude yellow oil obtained after evaporation of the solvent was purified by flash chromatography on silica gel eluted with petroleum ether/ethyl acetate (93:7): white solid (351 mg, 79%).

$^1$H-NMR (CDCl$_3$) δ: 8.30 (1H, ddd, J=0.76 Hz, J=1.88 Hz, J=8.50 Hz), 7.89 (1H, ddd, J=0.76 Hz, J=1.2 Hz, J=8.24 Hz) 7.82 (1H, d, J=8.80 Hz), 7.63 (1H, ddd, J=1.2 Hz, J=6.88 Hz, J=8.50 Hz), 7.55 (1H, ddd, J=1.88 Hz, J=6.88 Hz, J=8.24 Hz), 7.35 (1H, d, 8.88 Hz), 3.53 (3H, s) 3.49 (3H, s).

S-1-chloro-2-naphthyl-dimethylthiocarbamate

A solution of O-1-chloro-2-naphthyl-dimethylthiocarbamate (1.13 mmol, 300 mg) in 4 mL of NMP was irradiated by MW at 200° C. for 4 h. The reaction mixture was diluted in ether and washed with water. The organic layer was dried over anhydrous sodium sulfate. The crude yellow oil obtained after evaporation of solvent was purified by flash chromatography on silica gel eluted with petroleum ether/ethyl acetate (8:2): slightly yellow solid (203 mg, 68%).

$^1$H-NMR (CDCl$_3$) δ: 8.37 (1H, ddd, J=0.76 Hz, J=1.88 Hz, J=8.50 Hz), 7.87 (1H, ddd, J=0.76 Hz, J=1.2 Hz, J=8.24 Hz) 7.78 (1H, d, J=8.80 Hz), 7.68-7.56 (3H, m), 3.30-2.90 (6H, brs).

1-chloronaphthalene-2-thiol

A solution of the S-1-chloro-2naphthyl-dimethyl thiocarbamate (150 mg, 0.56 mmol) in 12.6 mL of KOH 0.3N in MeOH (4.68 mmol) was saturated with Argon and heated to 80° C. for 2.5 h. The reaction mixture was then quenched with aqueous HCl 1N (12 mL) at 0° C. and it was extracted with dichloromethane. The aqueous phase was washed with dichloromethane. The combined organic phases are washed with brine, dried over anhydrous sodium sulfate and evaporated affording the thiol as a yellow solid (90 mg; 83%).

$^1$H-NMR (CDCl$_3$) δ: 8.21 (1H, ddd, J=0.76 Hz, J=1.88 Hz, J=8.50 Hz), 7.81 (1H, ddd, J=0.76 Hz, J=1.2 Hz, J=8.24 Hz) 7.65 (1H, d, J=8.80 Hz), 7.61 (1H, ddd, J=1.2 Hz, J=6.88 Hz, J=8.50 Hz), 7.49 (1H, ddd, J=1.88 Hz, J=6.88 Hz, J=8.24 Hz), 7.40 (1H, d, J=8.88 Hz), 4.12 (1H, brs); GC-MS: m/z 194.6

2-[(1-chloronaphthalen-2-yl)sulfanyl]ethanaminium chloride

A solution of 1-chloronaphthalene-2-thiol (0.45 mmol, 88 mg) in 4 mL of acetone containing potassium carbonate (2.25 mmol, 311 mg) was stirred for 30 minutes (the colourless mixture turned to yellow) than tert-butyl (2-bromoethyl)carbamate (0.47 mmol, 105 mg) was added. The reaction was stirred at room temperature for 1 h. After total disappearance of starting material (monitored by TLC), the solvent was evaporated under reduced pressure. The residue was treated with dichloromethane and washed with water. The organic layer was dried over anhydrous sodium sulfate. The crude yellow oil obtained after evaporation of the solvent was purified by flash chromatography on silica gel eluted with petroleum ether/ethyl acetate (8:2): white solid (76 mg, 50%).

The obtained compound was dissolved in 4 mL of ethyl ether and 5 mL of 4 M HCl dioxane solution were added. The resulting mixture was stirred at room temperature for 18 h. The reaction mixture was concentrated under reduce pressure to afford 2-[(1-chloronaphthalen-2-yl)sulfanyl]ethanaminium chloride as a yellow oil (92% yield) which was pure by TLC and NMR analysis.

$^1$H-NMR (DMSO-d6) δ: 8.40-8.20 (3H, brs), 8.15 (1H, ddd, J=0.76 Hz, J=1.88 Hz, J=8.50 Hz), 8.07-7.96 (2H, m), 7.75-7.65 (2H, m), 7.58 (1H, ddd, J=1.88 Hz, J=6.88 Hz, J=8.24 Hz), 3.42 (2H, t, J=8.39 Hz) 3.06 (2H, t, J=8.39 Hz); HPLC-MS (ESI+): m/z 238.7 [M+H$^+$].

2-[(1-chloronaphthalen-2-yl)sulfanyl]-N-(furan-2-ylmethyl)ethanamine

The reductive amination step of 2-[(1-chloronaphthalen-2-yl)sulfanyl]ethanaminium chloride with furan-2-carbaldehyde was performed as described for compound I to obtain 2-[(1 chloronaphthalen-2-yl)sulfanyl]-N-(furan-2-ylmethyl) ethanamine in 57% yield.

$^1$H-NMR (CD$_3$OD) δ: 8.15 (1H, ddd, J=0.76 Hz, J=1.88 Hz, J=8.50 Hz), 7.90-7.75 (2H, m), 7.60-7.40 (4H, m), 3.42 (2H, t, J=8.39 Hz) 3.06 (2H, t, J=8.39 Hz); 6.49 (1H, dd, J=3.58) 6.32 (1H, dd, J=2.10 Hz, J=3.58 Hz) 4.22 (2H, s), 3.38 (2H, t, J=8.39 Hz) 3.23 (2H, t, J=8.39 Hz).

Synthesis of Compound

2-[(1-chloronaphthalen-2-yl)sulfonyl]-N-(furan-2-ylmethyl)ethanamine (25)

To a solution of m-CPBA (metachloroperbenzoic acid) (106 mg, 0.62 mmol) in dichloromethane (4 mL), cooled to 0° C., was added dropwise a solution of 2-[(1-chloronaphthalen-2-yl)sulfanyl]-N-(furan-2-ylmethyl)ethanamine (100 mg, 0.31 mmol) in dichloromethane (2 mL) over 3 min. The reaction mixture was stirred at room temperature for 4 h and then diluted with cold 4% sodium bicarbonate solution (4 mL). The organic layer was separated, washed with water, dried over anhydrous sodium sulfate and concentrated under reduced pressure. The crude residue was purified by silica gel column chromatography using petroleum ether/ethyl acetate (8:2): yellow solid (65 mg, 60%).

$^1$H-NMR (CD$_3$OD) δ: 8.16 (1H, ddd, J=0.76 Hz, J=1.88 Hz, J=8.50 Hz), 7.85-7.68 (2H, m), 7.60 (1H, ddd, J=1.2 Hz, J=6.88 Hz, J=8.50 Hz), 7.50-7.30 (3H, m), 6.81 (1H, dd, J=0.75 Hz, J=3.30 Hz) 6.44 (1H, dd, J=2.01 Hz, J=3.30 Hz), 4.10 (2H, s) 3.3-2.95 (4H, m);

HPLC-MS (ESI+): m/z 350.8 [M+H$^+$].

Following the same procedure described for the synthesis of compound 25, the following compounds have been synthesised:

Example 28

2-[(1-chloronaphthalen-2-yl)sulfonyl]-N-[(5-methyl-furan-2-yl)methyl]ethanamine (26)

Prepared as described for compound 25, from 2-[(1-chloronaphthalen-2-yl)sulfanyl]-N-[(5-methylfuran-2-yl)methyl]ethanamine in 59% yield as white solid.

¹H-NMR (CD₃OD) δ: 8.16 (1H, ddd, J=0.76 Hz, J=1.88 Hz, J=8.50 Hz), 7.85-7.68 (2H, m), 7.60 (1H, ddd, J=1.2 Hz, J=6.88 Hz, J=8.50 Hz), 7.50-7.30 (2H, m), 6.81 (1H, d, J=3.30 Hz) 6.44 (1H, qd, J=1.05 Hz, J=3.30 Hz), 4.10 (2H, s), 3.3-2.95 (4H, m), 2.33 (3H, d, J=0.9 Hz); HPLC-MS (ESI+): m/z 364.9 [M+H⁺].

Example 29

N-[(5-chlorofuran-2-yl)methyl]-2-[(1-chloronaphthalen-2-yl)sulfonyl]ethanamine (27)

Prepared as described for compound 25 from N-[(5-chlorofuran-2-yl)methyl]-2-[(1 chloronaphthalen-2-yl)sulfanyl] ethanamine in 50% yield as whitish solid.

¹H-NMR (CD₃OD) δ: 8.16 (1H, ddd, J=0.76 Hz, J=1.88 Hz, J=8.50 Hz), 7.85-7.68 (2H, m), 7.60 (1H, ddd, J=1.2 Hz, J=6.88 Hz, J=8.50 Hz), 7.50-7.30 (2H, m), 6.88 (1H, d, J=3.30 Hz) 6.46 (1H, d, J=3.30 Hz), 4.12 (2H, s), 3.32-2.95 (4H, m); HPLC-MS (ESI+): m/z 385.3 [M+H⁺].

Example 30

2-[(1-chloronaphthalen-2-yl)sulfonyl]-N-[(5-chlorothiophen-2-yl)methyl]ethanamine (28)

Prepared as described for compound 25 from 2-[(1-chloronaphthalen-2-yl)sulfanyl]-N-[(5-chlorothiophen-2-yl)methyl]ethanamine in 63% yield as whitish solid.

¹H-NMR (CD₃OD) δ: 8.16 (1H, ddd, J=0.76 Hz, J=1.88 Hz, J=8.50 Hz), 7.85-7.68 (2H, m), 7.60 (1H, ddd, J=1.2 Hz, J=6.88 Hz, J=8.50 Hz), 7.50-7.30 (2H, m), 6.93 (1H, d, J=3.30 Hz) 6.48 (1H, d, J=3.30 Hz), 4.12 (2H, s), 3.32-2.95 (4H, m);
HPLC-MS (ESI+): m/z 401.3 [M+H⁺].

Example 31

2-[(1-chloronaphthalen-2-yl)sulfonyl]-N-(thiophen-2-ylmethyl)ethanamine (29)

Prepared as described for compound 25 from 2-[(1-chloronaphthalen-2-yl)sulfanyl]-N-(thiophen-2-ylmethyl)ethanamine in 68% yield as yellow solid.

¹H-NMR (CD₃OD) δ: 8.16 (1H, ddd, J=0.76 Hz, J=1.88 Hz, J=8.50 Hz), 7.85-7.68 (2H, m), 7.60 (1H, ddd, J=1.2 Hz, J=6.88 Hz, J=8.50 Hz), 7.50-7.30 (3H, m), 6.81 (1H, dd, J=0.75 Hz, J=3.30 Hz) 6.44 (1H, dd, J=2.01 Hz, J=3.30 Hz), 4.25 (2H, s) 3.3-2.95 (4H, m); HPLC-MS (ESI+): m/z 366.9 [M+H⁺].

Example 32

2-[(1-chloronaphthalen-2-yl)sulfonyl]-N-(pyridin-2-ylmethyl)ethanamine (30)

Prepared as described for compound 25 from 2-[(1-chloronaphthalen-2-yl)sulfanyl]-N-(pyridin-2-ylmethyl)ethanamine in 78% yield as yellow oil.

¹H-NMR (CD₃OD) δ: 8.72 (1H, m), 8.20 (1H, ddd, J=0.76 Hz, J=1.88 Hz, J=8.50 Hz), 8.01 (1H, dd, J=1.70 Hz, J=7.78 Hz), 7.95-7.85 (2H, m), 7.75-7.68 (1H, m), 7.65-7.55 (2H, m), 7.52-7.42 (2H, m), 4.55 (2H, s) 3.3-2.95 (4H, m); HPLC-MS (ESI+): m/z 361.7 [M+H⁺].

Example 33

2-[(1-chloronaphthalen-2-yl)sulfonyl]-N-[(1-methyl-1H-pyrrol-2-yl)methyl]ethanamine (31)

Prepared as described for compound 25 from 2-[(1-chloronaphthalen-2-yl)sulfanyl]-N-[(1-methyl-1H-pyrrol-2-yl)methyl]ethanamine and in 76% yield as yellow oil.

¹H-NMR (CD₃OD) δ: 8.20 (1H, ddd, J=0.76 Hz, J=1.88 Hz, J=8.50 Hz), 7.93-7.83 (2H, m), 7.61 (1H, ddd, J=1.2 Hz, J=6.88 Hz, J=8.50 Hz), 7.52-7.40 (2H, m), 6.78 (1H, dd, J=1.80 Hz, J=2.60 Hz), 6.40 (1H, dd, J=1.80 Hz, J=3.72 Hz) 6.10 (1H, dd, J=2.60 Hz, J=3.72 Hz) 3.73 (3H, s), 3.61 (2H, t, J=5.60 Hz), 3.3-2.95 (4H, m); HPLC-MS (ESI+): m/z 363.7 [M+H⁺].

Example 34

Synthesis of 3-(1-chloronaphthalen-2-yl)-N-(furan-2-ylmethyl)propan-1-amine (32)

Preparation of Intermediates (2E)-3-(1-chloronaphthalen-2-yl)prop-2-enenitrile

Pd(OAc)₂ (3 mol %, 11 mg), PMe₂Ph (5 mol %, 11 mg), 1-chloronaphthalen-2-yl trifluoromethanesulfonate (500 mg, 1.61 mmol), acrylonitrile (103 mg, 1.93 mmoli), triethylamine (242 mg, 2.4 mmol) and 15 mL of acetonitrile were added to a microvawe vial and the mixture was irradiated by MW at 120° C. for 1 h. At the conclusion of the reaction, the solvent was evaporated under reduced pressure and the residue was treated with dichloromethane and washed with water; the organic layer was filtered through a pad of silica gel with copious washings, concentrated, and purified by flash chromatography on silica gel eluted with petroleum ether/ethyl acetate (93:7) to give (2E)-3-(1-chloronaphthalen-2-yl) prop-2-enenitrile as colourless oil (120 mg, 35% yield).

GC-MS: m/z 213.7.

3-(1-chloronaphthalen-2-yl)propan-1-amine

To a solution of (2E)-3-(lchloronaphthalen-2-yl)prop-2-enenitrile (120 mg, 0.56 mmol) in 5 mL of dry THF, LiAlH₄ (85 mg, 2.24 mmol) was added under argon atmosphere. The reaction was refluxed over night. After total disappearance of starting material the reaction mixture was quenched with aqueous HCl 1N at 0° C. until pH 5 and stirred at room temperature for 30 minutes, than neutralized with NaOH 1N and extracted with ethyl acetate. The organic layer was dried over anhydrous sodium sulfate and concentrated under reduced pressure to yield pure product as a yellow oil (92 mg, 75%).

¹H-NMR (CD₃OD) δ: 8.08 (1H, ddd, J=0.76 Hz, J=1.88 Hz, J=8.50 Hz), 7.80 (1H, ddd, J=0.76 Hz, J=1.2 Hz, J=8.24 Hz), 7.65 (1H, d, 8.88 Hz), 7.60 (1H, ddd, J=1.2 Hz, J=6.88 Hz, J=8.50 Hz), 7.41 (1H, ddd, J=1.88 Hz, J=6.88 Hz, J=8.24 Hz), 7.23 (1H, d, J=8.88 Hz); 3.17 (2H, m), 2.21 (2H, m), 1.5 (2H, m); HPLC-MS (ESI+): m/z 220.7 [M+H⁺].

Synthesis of Compound

3-(1-chloronaphthalen-2-yl)-N-(furan-2-ylmethyl)propan-1-amine (32)

The reductive ammination of 3-(1-chloronaphthalen-2-yl)propan-1-amine and furan-2-carbaldehyde was performed as described for compound I to obtain the compound as a pale yellow oil (45% yield).

$^1$H-NMR (CDCl$_3$) δ: 10.25 (2H, brs), 8.20 (1H, ddd, J=0.76 Hz, J=1.88 Hz, J=8.50 Hz), 7.80 (1H, ddd, J=0.76 Hz, J=1.2 Hz, J=8.24 Hz), 7.73 (1H, d, 8.88 Hz), 7.60 (1H, ddd, J=1.2 Hz, J=6.88 Hz, J=8.50 Hz), 7.50 (1H, dd, J=0.75 Hz, J=2.01 Hz) 7.45 (1H, ddd, J=1.88 Hz, J=6.88 Hz, J=8.2 Hz), 7.20 (1H, d, 8.88 Hz), 6.79 (1H, dd, J=0.75 Hz, J=3.30 Hz) 6.41 (1H, dd, J=2.01 Hz, J=3.30 Hz), 3.90 (2H, s), 3.29-3.10 (2H, m), 2.3-2.00 (2H, m) 1.3-1.1 (2H, m); HPLC-MS (ESI+): m/z 300.8 [M+H+].

Example 35

3-(1-chloronaphthalen-2-yl)-N-[(5-methylfuran-2-yl)methyl]propan-1-amine (33)

Prepared from 3-(1-chloronaphthalen-2-yl)propan-1-amine and 5-methylfuran-2-carbaldehyde in 89% yield as a pale yellow oil.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.56 (1H, d, J=3.37 Hz) 6.11 (1H, qd, J=0.9 Hz, J=3.37 Hz), 3.93 (2H, s), 3.29-3.10 (2H, m), 2.40-2.05 (5H, m) 1.3-1.1 (2H, m); HPLC-MS (ESI+): m/z 314.7 [M+H$^+$].

Example 36

N-[(5-chlorofuran-2-yl)methyl]-3-(1-chloronaphthalen-2-yl)propan-1-amine (34)

Prepared from 3-(1-chloronaphthalen-2-yl)propan-1-amine and 5-chlorofuran-2-carbaldehyde in 85% yield as a yellow oil.

$^1$H-NMR (CD$_3$OD) δ: 8.20 (1H, ddd, J=0.76 Hz, J=1.88 Hz, J=8.50 Hz), 7.95-7.85 (2H, m), 7.61 (1H, ddd, J=1.2 Hz, J=6.88 Hz, J=8.50 Hz), 7.52-7.44 (2H, m), 6.76 (1H, d, J=3.55 Hz) 6.39 (1H, d, J=3.35 Hz) 3.99 (2H, s), 3.29-3.10 (2H, m), 2.3-2.00 (2H, m) 1.3-1.1 (2H, m); HPLC-MS (ESI+): m/z 335.2 [M+H$^+$].

Example 37

3-(1-chloronaphthalen-2-yl)-N-[(5-chlorothiophen-2-yl)methyl]propan-1-amine (35)

Prepared from 3-(1-chloronaphthalen-2-yl)propan-1-amine and 5-chlorothiophen-2-carbaldehyde in 78% yield as a red oil.

$^1$H-NMR (CD$_3$OD) δ: 8.20 (1H, ddd, J=0.76 Hz, J=1.88 Hz, J=8.50 Hz), 7.92-7.85 (2H, m), 7.62 (1H, ddd, J=1.2 Hz, J=6.88 Hz, J=8.50 Hz), 7.52-7.44 (2H, m), 7.20 (1H, d, J=3.80 Hz) 7.02 (1H, d, J=3.80 Hz) 3.95 (2H, s), 3.29-3.10 (2H, m), 2.3-2.00 (2H, m) 1.3-1.1 (2H, m); HPLC-MS (ESI+): m/z 351.3 [M+H$^+$].

Example 38

3-(1-chloronaphthalen-2-yl)-N-(thiophen-2-ylmethyl)propan-1-amine (36)

Prepared from 3-(1-chloronaphthalen-2-yl)propan-1-amine and thiophen-2-carbaldehyde in 70% yield as a slightly red oil.

$^1$H-NMR (CDCl$_3$) δ: 8.20 (1H, ddd, J=0.76 Hz, J=1.88 Hz, J=8.50 Hz), 7.80 (1H, ddd, J=0.76 Hz, J=1.2 Hz, J=8.24 Hz), 7.73 (1H, d, 8.88 Hz), 7.60 (1H, ddd, J=1.2 Hz, J=6.88 Hz, J=8.50 Hz), 7.50 (1H, dd, J=0.75 Hz, J=2.01 Hz) 7.45 (1H, ddd, J=1.88 Hz, J=6.88 Hz, J=8.2 Hz), 7.20 (1H, d, 8.88 Hz), 6.83 (1H, dd, J=0.75 Hz, J=3.30 Hz) 6.43 (1H, dd, J=2.01 Hz, J=3.30 Hz), 3.99-3.87 (2H, s), 3.29-3.10 (2H, m), 2.3-2.00 (2H, m) 1.3-1.1 (2H, m); HPLC-MS (ESI+): m/z 316.9 [M+H$^+$].

Example 39

3-(1-chloronaphthalen-2-yl)-N-(pyridin-2-ylmethyl)propan-1-amine (37)

Prepared from 3-(1-chloronaphthalen-2-yl)propan-1-amine and pyridine-2-carbaldehyde in 67% yield as a yellow oil.

$^1$H-NMR (CD$_3$OD) δ: 8.72 (1H, m), 8.20 (1H, ddd, J=0.76 Hz, J=1.88 Hz, J=8.50 Hz), 8.01 (1H, dd, J=1.70 Hz, J=7.78 Hz), 7.95-7.85 (2H, m), 7.75-7.68 (1H, m), 7.65-7.55 (2H, m), 7.52-7.42 (2H, m), 4.55 (2H, s) 3.3-2.95 (4H, m), 2.3-2.00 (2H, m). HPLC-MS (ESI+): m/z 311.7 [M+H$^+$].

Example 40

2-[(1-chloronaphthalen-2-yl)oxy]-N-(furan-2-ylmethyl)-N-methylethanamine (38)

A solution (32 mg, 0.095 mmol) of 2-[(1-chloronaphthalen-2-yl)oxy]-N-(furan-2 ylmethyl)ethanaminium chloride (1) in 5 mL of THF was treated with 21 mg (0.15 mmol) of K$_2$CO$_3$ and 6 µL (0.100 mmol) of MeI. The resulting mixture was stirred for 14 h at room temperature. The solvent was distilled off under vacuum and the crude was triturated for 1 h in 5 mL of di-isopropyl ether. Pure 2-[(1-chloronaphthalen-2-yl)oxy]-N-(furan-2-ylmethyl)-N-methylethanamine was obtained after decantation of ether as a pale yellow oil in 91% yield.

$^1$H-NMR (CDCl$_3$) δ: 8.20 (1H, ddd, J=0.76 Hz, J=1.88 Hz, J=8.50 Hz), 7.80 (1H, ddd, J=0.76 Hz, J=1.2 Hz, J=8.24 Hz), 7.73 (1H, d, 8.88 Hz), 7.60 (1H, ddd, J=1.2 Hz, J=6.88 Hz, J=8.50 Hz), 7.50 (1H, dd, J=0.75 Hz, J=2.01 Hz) 7.45 (1H, ddd, J=1.88 Hz, J=6.88 Hz, J=8.2 Hz), 7.32 (1H, d, 8.88 Hz), 6.79 (1H, dd, J=0.75 Hz, J=3.30 Hz) 6.41 (1H, dd, J=2.01 Hz, J=3.30 Hz) 4.60 (2H, t, J=5.60 Hz), 4.53 (2H, m), 3.46 (2H, t, J=5.60 Hz), 3.1 (3H, s); HPLC-MS (ESI+): m/z 316.9 [M+H$^+$].

Example 41

2-[(1-chloronaphthalen-2-yl)oxy]-N-(furan-2-ylmethyl)-N,N-dimethylethanaminium iodide (39)

A solution of 2-[(1-chloronaphthalen-2-yl)oxy]-N-(furan-2-ylmethyl)-N-methylethanamine (38) (0.05 mmol) was dissolved in 3 mL of THF; then 0.10 mmol of MeI were added under stirring and allowed to react for 14 h at room temperature. The solvent was evaporated under vacuum and the resulting crude was triturated with 5 mL of n-hexane for 2 h. The solid was filtered and dried at 50° C. under reduce pressure to afford 2-[(1-chloronaphthalen-2-yl)oxy]-N-(furan-2-ylmethyl)-N,N-dimethylethanaminium iodide as a white solid (92% yield).

$^1$H-NMR (DMSO-d6) δ: 8.29 (1H, ddd, J=0.76 Hz, J=1.88 Hz, J=8.50 Hz), 7.85 (1H, ddd, J=0.76 Hz, J=1.2 Hz, J=8.24 Hz), 7.73 (1H, d, 8.88 Hz), 7.60 (1H, ddd, J=1.2 Hz, J=6.88 Hz, J=8.50 Hz), 7.50 (1H, dd, J=0.75 Hz, J=2.01 Hz) 7.45 (1H, ddd, J=1.88 Hz, J=6.88 Hz, J=8.2 Hz), 7.32 (1H, d, 8.88 Hz), 6.93 (1H, dd, J=0.75 Hz, J=3.30 Hz) 6.44 (1H, dd, J=2.01 Hz, J=3.30 Hz) 4.70-4.40 (4H, m), 4.53 (2H, m), 3.55 (2H, t, J=5.60 Hz), 3.1 (6H, s); HPLC-MS (ESI+): m/z 331.9 [M+H$^+$].

Example 42

Synthesis of N-(1-chloronaphthalen-2-yl)-N'-(furan-2-ylmethyl)ethane-1,2-diamine (41)

Preparation of Intermediates 1-chloronaphthalen-2-yl trifluoromethanesulfonate

To a solution of naphthalen-2-ol (0.5 g, 2.8 mmol) in 10 mL of dry CH$_2$Cl$_2$, triethylamine (0.6 mL 4.2 mmol) was added. The solution was cooled at −10° C. and triflic anhydride (0.5 mL, 3.1 mmol) was added dropwise; the reaction was stirred at −10° C. for 20 min and then allowed to stir at room temperature for 15 h. The mixture was quenched with 5 mL of 1M HCl solution, and transferred to a separatory funnel. The two phases were separated; the organic one was washed with 1N NaOH solution (5 mL), and dried over Na$_2$SO$_4$. After removal of the solvent, the residue was purified by flash chromatography (petroleum ether as eluent) to give 1-chloronaphthalen-2-yl trifluoromethanesulfonate as colourless oil (77% yield).

$^1$H-NMR (CDCl$_3$) δ: 8.34 (1H, ddd, J=0.76 Hz, J=1.88 Hz, J=8.50 Hz), 7.92 (1H, ddd, J=0.76 Hz, J=1.2 Hz, J=8.24 Hz), 7.86 (1H, d, 8.88 Hz), 7.71 (1H, ddd, J=1.2 Hz, J=6.88 Hz, J=8.50 Hz), 7.64 (1H, ddd, J=1.88 Hz, J=6.88 Hz, J=8.24 Hz), 7.46 (1H, d, 8.88 Hz);

GC-MS: m/z=310.7 tert-butyl {2-[(1-chloronaphthalen-2-yl)amino]ethyl}carbamate

An oven-dried microwave vial was evacuated and backfilled with argon. The vial was charged with Pd(OAc)$_2$ (25 mg 0.113 mmol, 10 mol % Pd), BINAP (112 mg, 0.17 mmol, 15 mol %), and Cs$_2$CO$_3$ (733 mg, 2.25 mmol) and evacuated and backfilled with argon. The flask was capped with a rubber septum, and dry dioxane (6 mL), 1-chloronaphthalen-2-yl trifluoromethanesulfonate (350 mg, 1.13 mmol), and tert-butyl (2-aminoethyl)carbamate (361 mg, 2.25 mmol) were added through the septum. Then, the reaction vial was sealed and placed in the microwave reactor and irradiated for 2 h at 150° C. until the starting materials had been completely consumed as judged by TLC and GC analysis. The crude product was purified by flash chromatography on silica gel (petroleum ether/ethyl acetate 99:1 to 90:10 as eluent) to afford tert-butyl {2-[(1-chloronaphthalen-2-yl)amino]ethyl}carbamate as a whitish solid in 48% yield.

$^1$H-NMR (Acetone-d6) δ: 7.94 (1H, ddd, J=0.76 Hz, J=1.88 Hz, J=8.50 Hz), 7.80-7.70 (2H, m), 7.48 (1H, ddd, J=1.2 Hz, J=6.88 Hz, J=8.50 Hz), 7.33-7.15 (2H, m), 6.42-6.20 (1H, brs), 5.60-5.40 (1H, brs), 3.53-3.44 (2H, m), 3.44-3.35 (2H, m), 1.4 (9H, s);

HPLC-MS (ESI+): m/z 321.8 [M+H$^+$].

2-[(1-chloronaphthalen-2-yl)amino]ethanaminium chloride

To a cooled (0° C.) single necked flask containing a solution of tert-butyl {2-[(1-chloronaphthalen-2-yl)amino]ethyl}carbamate in 4 mL of ethyl ether, 5 mL of 4 M HCl solution in dioxane were added. The resulting mixture was stirred at room temperature for 7 h. The reaction mixture was concentrated under reduce pressure to afford 2-[(1-chloronaphthalen-2-yl)amino]ethanaminium chloride as a pink solid (92% yield) which was pure by TLC and NMR analysis.

$^1$H-NMR (DMSO-d6) δ: 8.20-8.00 (3H, brs), 7.94 (1H, ddd, J=0.76 Hz, J=1.88 Hz, J=8.50 Hz), 7.85-7.80 (2H, m), 7.53 (1H, ddd, J=1.2 Hz, J=6.88 Hz, J=8.50 Hz), 7.34-7.25 (2H, m), 6.20-5.50 (1H, brs), 3.65-3.55 (2H, m), 3.10-2.95 (2H, m); HPLC-MS (ESI+): m/z 221.7 [M+H$^+$].

Synthesis of compound

N-(1-chloronaphthalen-2-yl)-N'-(furan-2-ylmethyl)ethane-1,2-diamine (41)

To a solution of 2-[(1-chloronaphthalen-2-yl)amino]ethanaminium chloride (73 mg, 0.25 mmol) in 4 mL of MeOH, K$_2$CO$_3$ (104 mg, 0.75 mmol) was added. After 10 min, 21 μL (0.253 mmol) of furan-2-carbaldehyde were added. The resulting solution was stirred for 2 h at room temperature, added with sodium borohydride (10 mg, 0.275 mmol) and the reaction was allowed to stir for further 15 h at rt. The mixture was diluted with 10 mL of ethyl acetate and transferred to a separatory funnel. The organic layer was washed with water and dried over anhydrous sodium sulfate, filtered, and concentrated in vacuo. The crude product was purified by flash chromatography on silica gel (CH$_2$Cl$_2$/MeOH 95:5 plus 0.3% NH$_4$OH) to afford N-(1-chloronaphthalen-2-yl)-N'-(furan-2-ylmethyl)ethane-1,2-diamine as a yellow oil (63% yield).

$^1$H-NMR (Acetone-d6) δ: 7.96 (1H, ddd, J=0.76 Hz, J=1.88 Hz, J=8.50 Hz), 7.80-7.70 (2H, m), 7.50 (1H, ddd, J=1.2 Hz, J=6.88 Hz, J=8.50 Hz), 7.44 (1H, dd, J=0.75 Hz, J=2.01 Hz) 7.30-7.18 (2H, m), 6.34 (1H, dd, J=0.75 Hz, J=3.30 Hz) 6.25 (1H, dd, J=2.01 Hz, J=3.30 Hz) 5.60-5.40 (1H, brs), 3.83 (2H, s) 3.50-3.35 (2H, m), 3.00-2.90 (2H, m), 2.80-2.60 (1H, brs); HPLC-MS (ESI+): m/z 301.6 [M+H$^+$].

The following compounds were prepared using the procedure described for compound (41):

Example 43

N-(1-chloronaphthalen-2-yl)-N'-[(5-methylfuran-2-yl)methyl]ethane-1,2-diamine (42)

Prepared from 2-[(1-chloronaphthalen-2-yl)amino]ethanaminium chloride and 5-methylfuran-2-carbaldehyde in 57% yield as a yellow oil.

$^1$H-NMR (Acetone-d6) δ: 7.96 (1H, ddd, J=0.76 Hz, J=1.88 Hz, J=8.50 Hz), 7.80-7.70 (2H, m), 7.50 (1H, ddd, J=1.2 Hz, J=6.88 Hz, J=8.50 Hz), 7.30-7.18 (2H, m), 6.50 (1H, d, Hz, J=3.30 Hz) 6.15 (1H, qd, J=1.00 Hz, J=3.30 Hz) 5.60-5.40 (1H, brs), 3.83 (2H, s) 3.50-3.35 (2H, m), 3.00-2.90 (2H, m), 2.80-2.60 (1H, brs), 2.31 (3H, d, J=1.00 Hz); HPLC-MS (ESI+): m/z 315.8 [M+H$^+$].

Example 44

N-[(5-chlorofuran-2-yl)methyl]-N'-(1-chloronaphthalen-2-yl)ethane-1,2-diamine (43)

Prepared from 2-[(1-chloronaphthalen-2-yl)amino]ethanaminium chloride and 5-chlorofuran-2-carbaldehyde in 67% yield as a yellow oil.

$^1$H-NMR (Acetone-d6) δ: 7.96 (1H, ddd, J=0.76 Hz, J=1.88 Hz, J=8.50 Hz), 7.80-7.70 (2H, m), 7.50 (1H, ddd, J=1.2 Hz, J=6.88 Hz, J=8.50 Hz), 7.30-7.18 (2H, m), 6.62 (1H, d, Hz, J=3.30 Hz) 6.30 (1H, d, J=3.30 Hz), 5.60-5.40 (1H, brs), 3.83 (2H, s) 3.55-3.35 (2H, m), 3.00-2.70 (2H, m), 2.80-2.60 (1H, brs); HPLC-MS (ESI+): m/z 336.2 [M+H$^+$].

Example 45

N-(1-chloronaphthalen-2-yl)-N'-[(5-chlorothiophen-2-yl)methyl]ethane-1,2-diamine (44)

Prepared from 2-[(1-chloronaphthalen-2-yl)amino]ethanaminium chloride and 5-chlorothiophene-2-carbaldehyde in 52% yield as a white oil.

$^1$H-NMR (Acetone-d6) δ: 7.96 (1H, ddd, J=0.76 Hz, J=1.88 Hz, J=8.50 Hz), 7.80-7.70 (2H, m), 7.50 (1H, ddd, J=1.2 Hz, J=6.88 Hz, J=8.50 Hz), 7.30-7.18 (2H, m), 6.78 (1H, d, Hz, J=3.30 Hz) 6.44 (1H, d, J=3.30 Hz), 5.63-5.48 (1H, brs), 3.84 (2H, s) 3.55-3.35 (2H, m), 3.10-2.70 (2H, m), 2.80-2.60 (1H, brs); HPLC-MS (ESI+): m/z 352.1 [M+H$^+$].

Example 46

N-(1-chloronaphthalen-2-yl)-N'-(thiophen-2-ylmethyl)ethane-1,2-diamine (45)

Prepared from 2-[(1-chloronaphthalen-2-yl)amino]ethanaminium chloride and thiophene-2-carbaldehyde in 59% yield as a white oil.

$^1$H-NMR (Acetone-d6) δ: 7.96 (1H, ddd, J=0.76 Hz, J=1.88 Hz, J=8.50 Hz), 7.80-7.70 (2H, m), 7.60-7.44 (2H, m), 7.30-7.18 (2H, m), 7.15-7.00 (1H, m), 6.78 (1H, dd, Hz, J=3.30 Hz, J=5.20 Hz) 6.44 (1H, d, J=3.30 Hz), 5.63-5.48 (1H, brs), 3.87 (2H, s) 3.55-3.35 (2H, m), 3.10-2.70 (2H, m), 2.80-2.60 (1H, brs); HPLC-MS (ESI+): m/z 317.6 [M+H$^+$].

Example 47

N-(1-chloronaphthalen-2-yl)-N'-(pyridin-2-ylmethyl)ethane-1,2-diamine (46)

Prepared from 2-[(1-chloronaphthalen-2-yl)amino]ethanaminium chloride and pyridine-2-carbaldehyde in 52% yield as a yellow oil.

$^1$H-NMR (Acetone-d6) δ: 8.68 (1H, m), 8.01 (1H, dd, J=1.70 Hz, J=7.78 Hz), 7.96 (1H, ddd, J=0.76 Hz, J=1.88 Hz, J=8.50 Hz), 7.95-7.85 (2H, m), 7.75-7.68 (1H, m), 7.65-7.55 (2H, m), 7.52-7.42 (2H, m), 5.68-5.50 (1H, brs), 3.99 (2H, s) 3.60-3.44 (2H, m), 3.10-2.70 (2H, m), 2.60-2.50 (1H, brs); HPLC-MS (ESI+): m/z 312.8 [M+H$^+$].

Example 48

N-(1-chloronaphthalen-2-yl)-N'-[(1-methyl-1H-pyrrol-2-yl)methyl]ethane-1,2-diamine (47)

Prepared from 2-[(1-chloronaphthalen-2-yl)amino]ethanaminium chloride and 1-methyl-1H-pyrrole-2-carbaldehyde in 47% yield as a white oil.

$^1$H-NMR (Acetone-d6) δ: 7.96 (1H, ddd, J=0.76 Hz, J=1.88 Hz, J=8.50 Hz), 7.80-7.70 (2H, m), 7.50 (1H, ddd, J=1.2 Hz, J=6.88 Hz, J=8.50 Hz), 7.30-7.18 (2H, m), 6.60 (1H, dd, J=1.80 Hz, J=2.60 Hz), 6.30 (1H, dd, J=1.80 Hz, J=3.72 Hz) 6.05 (1H, dd, J=2.60 Hz, J=3.72 Hz), 5.63-5.48 (1H, brs), 3.87 (2H, s) 3.55-3.35 (2H, m), 3.10-2.70 (2H, m), 2.80-2.60 (1H, brs); HPLC-MS (ESI+): m/z 314.6 [M+H$^+$].

Example 49

Synthesis of 2-[(1-fluoronaphthalen-2-yl)oxy]-N-(furan-2-ylmethyl)ethanamine (48)

Preparation of Intermediates 1-fluoronaphthalen-2-ol

To a cooled (0-5° C.) solution of NFSI (0.82 g, 2.6 mmol) in 30 mL of CH$_2$Cl$_2$, ZrCl$_4$ (0.031 g, 5% mol) was added followed by 0.375 g (2.6 mmol) of naphthalen-2-ol. The mixture was stirred for 18 h at room temperature until the complete disappearance of the starting material as judged by TLC and GC analysis. The mixture was quenched with saturated NaHCO$_3$ aqueous solution (30 mL) and transferred to a separatory funnel. The two phases were separated and the organic one was washed with water (3×10 mL), dried over Na$_2$SO$_4$ and evaporated under vacuum to give a yellow oil. The crude was purified by flash cromatography (petroleum ether/ethyl acetate 85:15) to afford 1-fluoronaphtalen-2-ol (0.214 g, 51% yield), as white solid.

$^1$H-NMR (CDCl$_3$) δ: 7.96 (1H, d), 7.83-7.77 (1H, m), 7.74-7.47 (2H, m), 7.44-7.38 (1H, m), 7.26-7.22 (1H, m). GC-MS: m/z 162.

tert-butyl {2-[(1-fluoronaphthalen-2-yl)oxy]ethyl}carbamate

To a solution of 1-fluoronaphthalen-2-ol (0.162 g, 1.0 mmol) and K$_2$CO$_3$ (0.300 g, 2.0 mmol) in acetone was added tert-butyl (2-bromoethyl)carbamate (0.336 g, 1.5 mmol). The resulting mixture was heated at reflux overnight. After TLC control (n-hexane/ethyl acetate 6:4) showed the disappearance of 1-fluoronaphthalen-2-ol, solvent was evaporated in vacuo and the residue was dissolved in 15 mL of ethyl acetate and washed with water (3×5 mL), brine (10 mL) and dried over Na$_2$SO$_4$. The evaporation of solvent afforded tert-butyl {2-[(1-fluoronaphthalen-2-yl)oxy]ethyl}carbamate as a white solid (65% yield) which was used without further purification.

$^1$H-NMR (CDCl$_3$) δ: 8.04 (1H, d), 7.83-7.77 (1H, m), 7.59 (1H, d), 7.52 (1H, t), 7.42 (1H, t), 7.29-7.24 (1H, m); 5.20-4.90 (1H, brs), 4.26 (2H, t, 5.1 Hz), 3.57 (2H, m, 5.1 Hz), 1.47 (9H, s).

2-[(1-fluoronaphthalen-2-yl)oxy]ethanaminium chloride

To a cooled (0° C.) single necked flask containing a solution of tert-butyl {2-[(1-fluoronaphthalen-2-yl)oxy]ethyl}carbamate in 5 mL of ethyl ether, 5 mL of 4 M HCl solution in dioxane were added. The resulting mixture was stirred at room temperature for 18 h. The reaction mixture was concentrated under reduce pressure to afford 2-[(1-fluoronaphthalen-2-yl)oxy]ethanaminium chloride as a white solid (95% yield) which was pure by TLC and NMR analysis.

¹H-NMR (CD₃OD) δ: 8.04 (1H, d), 7.83-7.76 (1H, m), 7.58 (1H, d), 7.52 (1H, t), 7.41 (1H, t), 7.32-7.27 (1H, m); 4.24 (2H, t, 5.1 Hz), 3.14 (2H, t, 5.1 Hz); HPLC-MS (ESI+): m/z 206 [M+H$^+$].

Synthesis of Compound

2-[(1-fluoronaphthalen-2-yl)oxy]-N-(furan-2-ylmethyl)ethanamine (48)

Prepared following the procedure used for compound (1) from 2-[(1-fluoronaphthalen-2-yl)oxy]ethanaminium chloride and furan-2-carbaldehyde in 65% yield as a white oil.

¹H-NMR (CD₃OD) δ: 8.00 (1H, d), 7.88-7.84 (1H, m), 7.70 (1H, d, J=8.88 Hz), 7.66 (1H, dd, J=0.75 Hz, J=2.01 Hz) 7.55 (1H, ddd, J=1.2 Hz, J=6.88 Hz, J=8.50 Hz), 7.46 (1H, ddd, J=1.88 Hz, J=6.88 Hz, J=8.2 Hz), 7.41 (1H, d, J=8.88 Hz), 6.70 (1H, dd, J=0.75 Hz, J=3.30 Hz) 6.52 (1H, dd, J=2.01 Hz, J=3.30 Hz) 4.49 (2H, t, J=5.1 Hz), 4.45 (2H, s) 3.51 (2H, t, J=5.1 Hz); HPLC-MS (ESI+): m/z 286.3 [M+H$^+$].

The following compounds were prepared using the procedure described for compound (48):

Example 50

2-[(1-fluoronaphthalen-2-yl)oxy]-N-[(5-methylfuran-2-yl)methyl]ethanamine (49)

Prepared from 2-[(1-fluoronaphthalen-2-yl)oxy]ethanaminium chloride and 5-methylfuran-2-carbaldehyde in 63% yield as a yellow oil. ¹H-NMR (CD₃OD) δ: 8.00 (1H, d), 7.88-7.84 (1H, m), 7.70 (1H, d, J=8.88 Hz), 7.55 (1H, ddd, J=1.2 Hz, J=6.88 Hz, J=8.50 Hz), 7.46 (1H, ddd, J=1.88 Hz, J=6.88 Hz, J=8.2 Hz), 7.41 (1H, d, J=8.88 Hz), 6.50 (1H, d, J=3.31 Hz) 6.14 (1H, qd, J=0.9 Hz, J=3.31 Hz) 4.47 (2H, t, J=5.00 Hz), 4.41 (2H, s) 3.50 (2H, t, J=5.00 Hz), 2.31 (3H, d, J=0.9 Hz).

HPLC-MS (ESI+): m/z 300.1 [M+H$^+$].

Example 51

N-[(5-chlorofuran-2-yl)methyl]-2-[(1-fluoronaphthalen-2-yl)oxy]ethanamine (50)

Prepared from 2-[(1-fluoronaphthalen-2-yl)oxy]ethanaminium chloride and 5-chlorofuran-2-carbaldehyde in 70% yield as a yellow oil.

¹H-NMR (CD₃OD) δ: 8.00 (1H, d), 7.88-7.84 (1H, m), 7.70 (1H, d, J=8.88 Hz), 7.55 (1H, ddd, J=1.2 Hz, J=6.88 Hz, J=8.50 Hz), 7.46 (1H, ddd, J=1.88 Hz, J=6.88 Hz, J=8.2 Hz), 7.41 (1H, d, J=8.88 Hz), 6.68 (1H, d, J=3.31 Hz) 6.35 (1H, d, J=3.31 Hz) 4.54-4.46 (4H, m) 3.50 (2H, t, J=5.00 Hz); HPLC-MS (ESI+): m/z 320.6 [M+H$^+$].

Example 52

N-[(5-chlorothiophen-2-yl)methyl]-2-[(1-fluoronaphthalen-2-yl)oxy]ethanamine (51)

Prepared from 2-[(1-fluoronaphthalen-2-yl)oxy]ethanaminium chloride and 5-chlorothiophen-2-carbaldehyde in 71% yield as a slightly white oil.

¹H-NMR (CD₃OD) δ: 8.00 (1H, d), 7.88-7.84 (1H, m), 7.70 (1H, d, J=8.88 Hz), 7.55 (1H, ddd, J=1.2 Hz, J=6.88 Hz, J=8.50 Hz), 7.46 (1H, ddd, J=1.88 Hz, J=6.88 Hz, J=8.2 Hz), 7.41 (1H, d, J=8.88 Hz), 7.20 (1H, d, J=3.80 Hz) 7.02 (1H, d, J=3.80 Hz), 4.56 (2H, s) 4.49 (2H, t, J=5.00 Hz), 3.50 (2H, t, J=5.00 Hz); HPLC-MS (ESI+): m/z 336.5 [M+H$^+$].

Example 53

2-[(1-fluoronaphthalen-2-yl)oxy]-N-(thiophen-2-ylmethyl)ethanamine (52)

Prepared from 2-[(1-fluoronaphthalen-2-yl)oxy]ethanaminium chloride and thiophen-2-carbaldehyde in 82% yield as a white oil.

¹H-NMR (CD₃OD) δ: 8.00 (1H, d), 7.88-7.84 (1H, m), 7.70 (1H, d, J=8.88 Hz), 7.60 (1H, ddd, J=1.2 Hz, J=6.88 Hz, J=8.50 Hz), 7.50-7.44 (2H, m), 7.40-7.30 (2H, m), 7.18 (1H, dd, J=3.80 Hz, J=5.30 Hz), 4.56 (2H, s) 4.49 (2H, t, J=5.00 Hz), 3.50 (2H, t, J=5.00 Hz).

HPLC-MS (ESI+): m/z 302.3 [M+H$^+$].

Example 54

2-[(1-fluoronaphthalen-2-yl)oxy]-N-(pyridin-2-ylmethyl)ethanamine (53)

Prepared from 2-[(1-fluoronaphthalen-2-yl)oxy]ethanaminium chloride and pyridine-2-carbaldehyde in 46% yield as a yellow oil.

¹H-NMR (CD₃OD) δ: 8.72 (1H, m), 8.20-7.90 (2H, m), 7.88-7.84 (1H, m), 7.70 (1H, d, J=8.88 Hz), 7.60 (1H, ddd, J=1.2 Hz, J=6.88 Hz, J=8.50 Hz), 7.50-7.44 (3H, m), 7.40-7.30 (3H, m), 4.66 (2H, s) 4.54 (2H, t, J=5.00 Hz), 3.59 (2H, t, J=5.00 Hz); HPLC-MS (ESI+): m/z 297.4 [M+H$^+$].

Example 55

2-[(1-fluoronaphthalen-2-yl)oxy]-N-[(1-methyl-1H-pyrrol-2-yl)methyl]ethanamine (54)

Prepared from 2-[(1-fluoronaphthalen-2-yl)oxy]ethanaminium chloride and 1-methyl-1H-pyrrole-2-carbaldehyde in 65% yield as a yellow oil.

¹H-NMR (CD₃OD) δ: 8.00 (1H, d), 7.88-7.84 (1H, m), 7.70 (1H, d, J=8.88 Hz), 7.60 (1H, ddd, J=1.2 Hz, J=6.88 Hz, J=8.50 Hz), 7.50-7.44 (2H, m), 7.40-7.30 (2H, m), 6.80 (1H, dd, J=1.75 Hz, J=2.60 Hz), 6.40 (1H, dd, J=1.75 Hz, J=3.72 Hz) 6.10 (1H, dd, J=2.60 Hz, J=3.72 Hz) 4.55-4.45 (4H, m), 3.70 (3H, s), 3.66 (2H, t, J=5.58 Hz); HPLC-MS (ESI+): m/z 299.3 [M+H$^+$].

Example 56

Synthesis of 5-chloro-6-{2-[(pyridin-2-ylmethyl)amino]ethoxy}naphthalene-2-carbonitrile (55)

Preparation of Intermediates 5-chloro-6-hydroxynaphthalene-2-carbonitrile

To a cooled (0° C.) solution of N-chlorosuccinimide (1.4 g, 10.4 mmol) in 80 mL of CH₂Cl₂, ZrCl₄ (0.122 g, 5% mol) was added, followed by 6-hydroxynaphthalene-2-carbonitrile (1.76 g, 10.4 mmol). The mixture was stirred for 18 h at room temperature until the complete disappearance of the starting material as judged by GC analysis. The mixture was quenched with saturated NH₄Cl aqueous solution (30 mL) and transferred to a separatory funnel. The two phases were separated and the organic one was washed with water (3×10 mL), dried over Na₂SO₄ and evaporated under vacuum to give a yellow oil. The crude was purified by flash cromatography (petroleum ether/ethyl acetate 75:25) to afford 5-chloro-6-hydroxynaphthalene-2-carbonitrile (1.38 gr, 65% yield), as whitish solid.

$^1$H-NMR (CD$_3$OD) δ: 8.40 (1H, d, J=1.88 Hz), 8.29 (1H, d, J=8.70 Hz), 8.05 (1H, d, J=8.50 Hz), 7.76 (1H, dd, J=1.88 Hz, J=8.7 Hz), 6.75 (1H, d, J=0.75 Hz, J=3.30 Hz);

GC-MS: m/z 203.5 tert-butyl {2-[(1-chloro-6-cyanonaphthalen-2-yl)oxy]ethyl}carbamate

To a solution of 5-chloro-6-hydroxynaphthalene-2-carbonitrile (1.5 mmol) and K$_2$CO$_3$ (3 mmol) in acetone was added tert-butyl (2-bromoethyl)carbamate (2.1 mmol). The resulting mixture was heated at reflux overnight. After TLC control (n-hexane/ethyl acetate 65:35), solvent was evaporated in vacuo and the residue was dissolved in 15 mL of ethyl acetate and washed with water (3×5 mL), brine (10 mL) and dried over Na$_2$SO$_4$. The evaporation of solvent afforded tert-butyl {2-[(1-chloro-6-cyanonaphthalen-2-yl)oxy]ethyl}carbamate as a brown solid (81% yield) which was used without further purification.

$^1$H-NMR (CD$_3$OD) δ: 8.51 (1H, d, J=1.88 Hz), 8.28 (1H, d, J=8.70 Hz), 8.04 (1H, d, J=8.50 Hz), 7.70 (1H, dd, J=1.88 Hz, J=8.7 Hz), 6.75 (1H, d, J=0.75 Hz, J=3.30 Hz), 5.20-4.85 (1H, brs), 4.60 (2H, t, J=5.60 Hz), 4.44 (2H, s), 1.39 (9H, s); HPLC-MS (ESI+): m/z=347.6 [M+H$^+$].

2-[(1-chloro-6-cyanonaphthalen-2-yl)oxy]ethanaminium chloride

To a cooled (0° C.) single necked flask containing a solution of tert-butyl {2-[(1-chloro-6-cyanonaphthalen-2-yl)oxy]ethyl}carbamate in 3 mL of ethyl ether, 5 mL of 4 M HCl solution in dioxane were added. The resulting mixture was stirred at room temperature overnight. The solution was concentrated under reduce pressure to afford 2-[(1-chloro-6-cyanonaphthalen-2-yl)oxy]ethanaminium chloride as a white solid (95% yield).

$^1$H-NMR (CD$_3$OD) δ: 8.43 (1H, d, J=1.88 Hz), 8.20 (1H, d, J=8.70 Hz), 8.06 (1H, d, J=8.50 Hz), 7.80 (1H, dd, J=1.88 Hz, J=8.7 Hz), 6.71 (1H, d, J=0.75 Hz, J=3.30 Hz), 4.40 (2H, t, J=5.60 Hz), 4.30 (2H, s); HPLC-MS (ESI+): m/z 247.7 [M+H$^+$]

Example 56

5-chloro-6-{2-[(pyridin-2-ylmethyl)amino]ethoxy}naphthalene-2-carbonitrile (55)

Prepared following the procedure used for compound (1) from 2-[(1-chloro-6-cyanonaphthalen-2-yl)oxy]ethanaminium chloride and pyridin-2-carbaldehyde in 56% yield as a slightly white solid.

$^1$H-NMR (CD$_3$OD) δ: 8.72 (1H, m), 8.41 (1H, d), 7.95-7.84 (2H, m), 7.75-7.68 (1H, m), 7.65-7.55 (2H, m), 7.52-7.42 (2H, m), 7.40-7.30 (1H, m), 4.72 (2H, s) 4.61 (2H, t, J=5.60 Hz), 3.71 (2H, t, J=5.00 Hz); HPLC-MS (ESI+): m/z 338.6 [M+H$^+$].

The following compounds were prepared using the procedure described for compound (55):

Example 57

5-chloro-6-{2-[(furan-2-ylmethyl)amino]ethoxy}naphthalene-2-carbonitrile (56)

Prepared from 2-[(1-chloro-6-cyanonaphthalen-2-yl)oxy]ethanaminium chloride and furan-2-carbaldehyde in 78% yield as a white solid.

$^1$H-NMR (CD$_3$OD) δ: 8.41 (1H, d, J=1.88 Hz), 8.34 (1H, d, J=8.70 Hz), 8.05 (1H, d, J=8.50 Hz) 7.78 (1H, dd, J=1.88 Hz, J=8.70 Hz), 7.69-7.50 (2H, m), 6.85 (1H, dd, J=0.75 Hz, J=3.30 Hz) 6.50 (1H, dd, J=2.01 Hz, J=3.30 Hz) 4.50 (2H, t, J=5.77 Hz), 4.30 (2H, s), 3.48 (2H, t, J=5.77 Hz); HPLC-MS (ESI+): m/z 327.8 [M+H$^+$].

Example 58

5-chloro-6-(2-{[(5-methylfuran-2-yl)methyl]amino}ethoxy)naphthalene-2-carbonitrile (57)

Prepared from 2-[(1-chloro-6-cyanonaphthalen-2-yl)oxy]ethanaminium chloride and 5-methylfuran-2-carbaldehyde in 77% yield as a slightly white solid.

$^1$H-NMR (CD$_3$OD) δ: 8.41 (1H, d, J=1.88 Hz), 8.34 (1H, d, J=8.70 Hz), 8.05 (1H, d, J=8.50 Hz), 7.78 (1H, dd, J=1.88 Hz, J=8.70 Hz), 7.64 (1H, d, J=8.50 Hz), 6.49 (1H, d, J=3.39 Hz) 6.11 (1H, qd, J=1.10 Hz, J=3.39 Hz) 4.60 (2H, t, J=5.60 Hz), 4.44 (2H, s), 3.53 (2H, t, J=5.60 Hz), 2.31 (3H, d, J=1.10 Hz); HPLC-MS (ESI+): m/z 341.8 [M+H$^+$].

Example 59

5-chloro-6-(2-{[(5-chlorofuran-2-yl)methyl]amino}ethoxy)naphthalene-2-carbonitrile (58)

Prepared from 2-[(1-chloro-6-cyanonaphthalen-2-yl)oxy]ethanaminium chloride and 5-chlorofuran-2-carbaldehyde in 60% yield as a yellow oil.

$^1$H-NMR (CD$_3$OD) δ: 8.41 (1H, d, J=1.88 Hz), 8.34 (1H, d, J=8.70 Hz), 8.05 (1H, d, J=8.50 Hz), 7.78 (1H, dd, J=1.88 Hz, J=8.70 Hz), 7.64 (1H, d, J=8.50 Hz), 6.69 (1H, d, J=3.39 Hz) 6.50 (1H, d, J=3.39 Hz) 4.60 (2H, t, J=5.60 Hz), 4.44 (2H, s), 3.53 (2H, t, J=5.60 Hz); HPLC-MS (ESI+): m/z 362.2 [M+H$^+$].

Example 60

5-chloro-6-(2-{[(5-chlorothiophen-2-yl)methyl]amino}ethoxy)naphthalene-2-carbonitrile (59)

Prepared from 2-[(1-chloro-6-cyanonaphthalen-2-yl)oxy]ethanaminium chloride and 5 chlorothiophen-2-carbaldehyde in 63% yield as a yellow solid.

$^1$H-NMR (CD$_3$OD) δ: 8.41 (1H, d, J=1.88 Hz), 8.34 (1H, d, J=8.70 Hz), 8.05 (1H, d, J=8.50 Hz), 7.78 (1H, dd, J=1.88 Hz, J=8.70 Hz), 7.64 (1H, d, J=8.50 Hz), 6.95 (1H, d, J=3.42 Hz) 6.60 (1H, d, J=3.42 Hz) 4.60 (2H, t, J=5.60 Hz), 4.44 (2H, s), 3.53 (2H, t, J=5.60 Hz); HPLC-MS (ESI+): m/z 378.2 [M+H$^+$].

Example 61

5-chloro-6-{2-[(thiophen-2-ylmethyl)amino]ethoxy}naphthalene-2-carbonitrile (60)

Prepared from 2-[(1-chloro-6-cyanonaphthalen-2-yl)oxy]ethanaminium chloride and thiophen-2-carbaldehyde in 35% yield as a whitish solid.

$^1$H-NMR (CD$_3$OD) δ: 8.41 (1H, d, J=1.88 Hz), 8.34 (1H, d, J=8.70 Hz), 8.05 (1H, d, J=8.50 Hz), 7.78 (1H, dd, J=1.88 Hz, J=8.70 Hz), 7.72-7.64 (2H, m), 6.95 (1H, d, J=0.75 Hz, J=3.30 Hz), 6.60 (1H, dd, J=2.01 Hz, J=3.30 Hz), 4.60 (2H, t, J=5.60 Hz), 4.44 (2H, s), 3.53 (2H, t, J=5.60 Hz); HPLC-MS (ESI+): m/z 343.8 [M+H$^+$].

Example 62

2-[(1-ethylnaphthalen-2-yl)oxy]-N-(furan-2-ylmethyl)ethanamine (61)

A single neck round-bottom flask was charged with 2.3 g of zinc, 0.23 g of HgCl$_2$ and 4 mL of water. Then 37% HCl (0.1 mL) was added and the mixture stirred for 5 minutes. After this, 3 mL of toluene and 3.4 mL of 37% HCl were added and finally 1 g (5.37 mmol) of 1-(2-hydroxynaphthalen-1-yl)ethanone was added portion wise. The resulting mixture was heated at 110° C. for 18 h. The phases were separated and the organic layer was dried over anhydrous sodium sulfate, filtered, and concentrated in vacuo to afford 780 mg (84% yield) of 1-ethylnaphthalen-2-ol as brown solid.

To a solution of 1-ethylnaphthalen-2-ol (780 mg, 4.53 mmol) and K$_2$CO$_3$ (626 mg, 4.53 mmol) in 15 mL of acetonitrile was added tert-butyl (2-bromoethyl)carbamate (1.015 g, 4.53 mmol). The resulting mixture was heated at reflux overnight. After TLC control (n-hexane/ethyl acetate 7:3) showed the disappearance of 1-ethylnaphthalen-2-ol, solvent was evaporated in vacuo and the residue was dissolved in 15 mL of ethyl acetate and washed with water (3×5 mL), brine (5 mL) and dried over Na2SO4. The evaporation of solvent afforded tert-butyl {2-[(1-ethylnaphthalen-2-yl)oxy]ethyl}carbamate which was dissolved in 10 mL of 4M HCl in dioxane and stirred for 1 h. The solvent was removed under vacuum and the residue was diluted with n-hexane (20 mL) and triturated at room temperature for 2 h. The solid was filtered and dried under vacuum at 50° C. to afford 2-[(1-ethylnaphthalen-2-yl)oxy]ethanaminium chloride as brown solid (821 mg, 72% yield). To a solution of 2-[(1-ethylnaphthalen-2-yl)oxy]ethanaminium chloride (100 mg, 0.397 mmol) in 10 mL of MeOH, K$_2$CO$_3$ (65 mg, 0.47 mmol) was added. After 10 min, 48 μL (0.58 mmol) of furan-2-carbaldehyde were added. The resulting solution was stirred for 1 h at room temperature, added with sodium borohydride (15 mg, 0.397 mmol) and allowed to stir for further 2 h at room temperature. The solvent was evaporated under vacuum. The crude product was purified by flash chromatography on silica gel (CH$_2$Cl$_2$/MeOH 97:3) to afford 2-[(1-ethylnaphthalen-2-yl)oxy]-N-(furan-2-ylmethyl)ethanamine as a brown solid (91 mg, 78% yield).

$^1$H-NMR (CD3OD) δ: 8.03 (1H, d, J=8.65 Hz), 7.87 (1H, d, J=7.87 Hz), 7.77 (1H, d, J=8.65 Hz), 7.72-7.66 (1H, m), 7.55-7.48 (1H, m), 7.42-7.32 (2H, m), 6.73 (1H, d, J=3.05 Hz), 6.56 (1H, dd, J=1.94 Hz, J=3.05 Hz), 4.49 (2H, s), 4.43 (2H, d, J=5.44 Hz), 3.57 (2H, d, J=5.44 Hz), 3.20 (2H, q, J=7.38 Hz), 1.27 (3H, t, J=7.38 Hz). HPLC-MS (ESI+): m/z 296.11 [M+H+].

Example 63

2,2-difluoro-2-[(1-fluoronaphthalen-2-yl)oxy]-N-(furan-2-ylmethyl)ethanamine (62)

To a solution of 1-(furan-2-yl)methanamine (1 g, 10.3 mmol) in 15 mL of dry DMF, ethyl bromo(difluoro)acetate (2.3 g, 11.3 mmol) and K$_2$CO$_3$ (2.13 g, 15.4 mmol) were added. The solution was stirred for 18 h at room temperature. The mixture was diluted with 30 mL of water and extracted with 2×20 mL of ethyl acetate. The organic layer was dried over anhydrous sodium sulfate, filtered, and concentrated in vacuo to afford 2-bromo-2,2-difluoro-N-(furan-2-ylmethyl)acetamide as red oil (2.3 g, 88% yield). HPLC-MS (ESI+): m/z 255.03 [M+H+].

To a solution of 1-fluoronaphthalen-2-ol (280 mg, 1.73 mmol) and K$_2$CO$_3$ (1.2 g, 8.65 mmol) in 10 mL of acetone, 2-bromo-2,2-difluoro-N-(furan-2-ylmethyl)acetamide (527 mg, 2.08 mmol) were added. The resulting mixture was stirred at 40° C. overnight. The reaction was cooled at room temperature, diluted with ethyl acetate (30 mL) and washed with water. The organic layer was dried over anhydrous sodium sulfate, filtered, and concentrated in vacuo to afford 2,2-difluoro-2-[(1-fluoronaphthalen-2-yl)oxy]-N-(furan-2-ylmethyl)acetamide as red oil (650 mg) which was used in the next step without further purification.

A microwave vial was charged with 2,2-difluoro-2-[(1-fluoronaphthalen-2-yl)oxy]-N-(furan-2-ylmethyl)acetamide (60 mg, 0.18 mmol), sodium borohydride (16 mg, 0.41 mmol) and 2 mL of dry THF. To this mixture, a solution of I2 (51 mg, 0.20 mmol) in 1 mL of dry THF was added. The vial was sealed and placed in the microwave reactor and irradiated for 30 min at 110° C. until the starting materials had been completely consumed as judged by TLC (petroleum ether/ethyl acetate 80:20). The mixture was evaporated under reduced pressure and the crude was purified by preparative HPLC to afford 2,2-difluoro-2-[(1-fluoronaphthalen-2-yl)oxy]-N-(furan-2-ylmethyl)ethanamine as orange oil (53 mg, 91% yield).

$^1$H-NMR (CD3OD) δ: 8.10 (1H, d, J=8.20 Hz), 7.95 (1H, d, J=8.20 Hz), 7.75-7.55 (3H, m), 7.52-7.42 (2H, m), 6.40 (1H, dd, J=2.00 Hz, J=3.16 Hz), 6.34 (1H, dd, J=0.80 Hz, J=3.16 Hz), 3.97 (2H, s), 3.33 (2H, m). HPLC-MS (ESI+): m/z 322.21 [M+H+].

Example 64

2-[(6-bromo-1-fluoronaphthalen-2-yl)oxy]-N-(furan-2-ylmethyl)ethanamine (63)

To a solution of 400 mg (2.24 mmol) of 1-chloronaphthalen-2-ol in 3 mL of MeOH, HBr (purum p.a., ≥62%, 270 μL) and H$_2$O$_2$ (50 wt. % in water solution, 27 μL) were added. The resulting mixture was heated at 40° C. and stirred overnight. The mixture was quenched with water (10 mL) and extracted with ethyl acetate (10 mL×2). The organic layer was dried over anhydrous sodium sulfate, filtered, and concentrated in vacuo to afford 6-bromo-1-chloronaphthalen-2-ol as pale yellow solid which was used in the next step without further purification. HPLC-MS (ESI+): m/z 258.51 [M+H+].

To a solution of 6-bromo-1-chloronaphthalen-2-ol (100 mg, 0.39 mmol) and K$_2$CO$_3$ (108 mg, 0.78 mmol) in 4 mL of acetonitrile was added tert-butyl (2-bromoethyl)carbamate (175 mg, 0.78 mmol). The resulting mixture was heated at 60° C. for 2 h. After TLC control (n-hexane/ethyl acetate 90:10) showed the disappearance of 6-bromo-1-chloronaphthalen-2-ol, solvent was evaporated in vacuo and the crude was taken up in 10 mL of 4M HCl in dioxane and stirred for 1 h. The solvent was removed under vacuum and the residue was diluted with n-hexane (10 mL) and triturated at room temperature overnight. The solid was filtered and dried under vacuum at 50° C. to afford 2-[(6-bromo-1-chloronaphthalen-2-yl)oxy]ethanaminium chloride as white solid (91 mg, 69% yield). HPLC-MS (ESI+): m/z 337.83 [M+H+].

To a solution of 2-[(6-bromo-1-chloronaphthalen-2-yl)oxy]ethanaminium chloride (91 mg, 0.27 mmol) in 10 mL of MeOH, $K_2CO_3$ (41 mg, 0.30 mmol) was added. After 10 min, 45 µL (0.54 mmol) of furan-2-carbaldehyde were added. The resulting solution was stirred for 1 h at room temperature, added with sodium borohydride (10 mg, 0.27 mmol) and then stirred for further 2 h at room temperature. The solvent was evaporated under vacuum and the crude product was purified by flash chromatography on silica gel ($CH_2Cl_2$/MeOH 95:5) to afford 2-[(6-bromo-1-chloronaphthalen-2-yl)oxy]-N-(furan-2-ylmethyl)ethanamine as a brown solid (87 mg, 85% yield). $^1$H-NMR (DMSO-d6) δ: 8.35 (1H, d, J=2.05 Hz), 8.07 (1H, d, J=9.01 Hz), 8.00 (1H, d, J=9.01 Hz), 7.81 (1H, dd, J=1.05 Hz, J=2.08 Hz), 7.78 (1H, dd, J=2.05 Hz, J=8.98 Hz), 7.67 (1H, d, J=8.98 Hz), 6.70 (1H, dd, J=1.05 Hz, J=3.34 Hz), 6.34 (1H, dd, J=2.08 Hz, J=3.34 Hz), 4.55 (2H, d, J=5.44 Hz), 4.43 (2H, s), 3.43 (2H, d, J=5.44 Hz). HPLC-MS (ESI+): m/z 381.21 [M+H+].

Example 65

Evaluation of in vitro Activity a. Cloning, Sequencing, Transfection and Selection of Positive Clones Expressing Human TRPM8

A functional cell-based assay for the identification of TRPM8 receptor antagonists, optimised to allow high throughput screening at FLIPR$^{TETRA}$, was developed in HEK293 cells by stable pure clone selection and functional characterization with a fluorescent calcium sensitive dye.

TRPM8 was cloned into the multiple clonig site of pcDNA3 mammalian expression vector; the obtained construct pcDNA3/hTRPM8 was fully sequence verified and used for the transfection of HEK293 cell line. HEK293 cells stably transfected with TRPM8 gene were maintained in Minimum essential medium. The cells were transfected with the pcDNA3/hTRPM8 vector by electroporation and then selected with medium containing 0.8 mg/ml G418 for 10-15 days.

The following commercial compounds were used as TRPM8 channel reference compound to test HEK293/hTRPM8 cell line for both agonist and antagonist activity:
Activators: Menthol (SIGMA cat.# M2772) WS-3, (N-Ethyl-5-methyl-2-(1-methylethyl)cyclohexanecarboxamide) (SIGMA cat.# W345501)
Blocker: Capsazepine (SIGMA cat.# C191)

The experimental activities were performed using FLIPR instruments.

The functional clones were selected at FLIPR$^{384}$ on the basis of 1 mM menthol response.

Two best responder clones were selected, diluted at a cell density of 1 cell/well and analysed at FLIPR$^{384}$ with 1 mM menthol.

The TRPM8 receptor was analysed for the response to reference agonist, menthol, using a calcium-dependent fluorescence signal.

Patch clamp recordings were also obtained in voltage-clamp configuration on HEK/TRPM8 clones in order to verify the receptor pharmacology and to determine the agonist dose-response curve and $EC_{50}$ value. HEK293 cells were maintained at room temperature on an fire-polished borosilicate glass pipettes having 1.5-2.5 MΩ resistance were used to record currents following drug application. Menthol application induced a dose-dependent inward current in a selected HEK/hTRPM8 clone (calculated $EC_{50}$ value=58 µM). No menthol-induced currents were recorded in non transfected HEK293 cells. In order to determine the capsazepine antagonist activity on menthol agonist response and to verify the antagonist response stability throughout different days of experiments, the selected clone of TRPM8 was analysed after 24 h at FLIPR$^{384}$ in presence of variable concentrations of antagonist (from 100 nM to 316 µM). The selected clone showed very good stability and reproducibility of the antagonist activity (calculated $IC_{50}$ value=20 µM).

Summarizing, the best clone was characterized for:
1—pharmacology: agonist $EC_{50}$ and antagonist $IC_{50}$ determination over different experiments;
2—optimal cell density and seeding time;
3—DMSO sensitivity;
4—ligand stability;
5—patch clamp analysis.

b. Screening Set Up for the Identification of TRPM8 Antagonists

The following commercial compounds were used as ligands:
Activator: Cooling Agent 10 (Takasago CAS N. 87061-04-9)
Blocker: Capsazepine (SIGMA cat #D_5879)

The experimental activities were performed using FLIPR$^{TETRA}$ instruments.

HEK293 cells stably transfected with TRPM8 gene were maintained in Minimum essential medium.

The TRPM8 cell line was analysed for the response to a library of compounds using a $Ca^{2+}$ mobilization-dependent fluorescence signal in 384 wells microtiter plate format. The analysis was performed using the FLIPR$^{TETRA}$ (MDC) with the ICCD Camera.

The execution of the assay involved the use of three microtiter plates:

1. Assay plate, containing cells loaded with dye and prepared as follows:

Cells were seeded at 15000 c/well in Poly-D-Lysine coated 384 wells Microtiter Plates in complete medium (25 µl/well).

24 h after seeding, the cell plates were washed with Tyrode assay buffer by the Microplate Washer and 10 µL of Tyrode assay buffer was left in each well.

Cells were then loaded with 10 µL/well of the Fluo-4 NW dye solution by CyBi®-Well pipettor. Each bottle of Fluo4-NW dye (Molecular Probes cat. #F36206, component A) was re-suspended in 8 mL of Tyrode assay buffer and supplemented with 100 µL of water-soluble probenecid (MolecularProbes cat.#F36206, component B).

Dye loaded cell plates were incubated for 1 h at room temperature.

2. Compound Dilution Plate (FIG. 1), containing diluted test compounds, formulated as follows:
Column 1: wells containing Assay Buffer plus DMSO 0.5% final
Column 2: wells alternating Max Signal Control in first injection (Maximum Response: Cooling Agent 10 at $EC_{100}$, 100 µM) and Min Signal Control in first injection (Assay buffer plus 0.5% DMSO final);
Columns 3-22: wells containing Assay Buffer plus 0.5% DMSO final. To these wells the compounds to be tested were added at 3× concentration.
Column 23: alternating wells of Max Signal Control in second injection (Assay buffer) and Min Signal Control in second injection (Antagonist Capsazepine $IC_{100}$, 50 µM) in Assay buffer plus 0.5% DMSO final;

Column 24: wells containing Capsazepine (Antagonist) at 8 concentrations in duplicate at final concentrations of 50 µM, 25 µM, 6.25 µM, 3.15 µM, 1.56 µM, 780 nM, 309 nM in Assay buffer plus 0.5% DMSO final.

3. Activator Plate (FIG. 2), containing agonist Cooling Agent 10 at EC80, formulated as follows:

Column 1: Cooling Agent 10 (Agonist) at 8 concentrations dose response in duplicate at final concentrations of 100 µM, 31.6 µM, 10 µM, 3.16 µM, 316 nM, 100 nM, 31.6 nM in Assay buffer;

Columns 2-24: Cooling Agent 10 (Agonist) at $EC_{80}$ (3 fold concentrated, 20 µM final) in Assay buffer.

The test was carried out according to a procedure comprising the following steps:

1. The samples contained in the wells of the Compound Plate were added to the corresponding wells of the Assay Plate by the FLIPR$^{TETRA}$, thus resulting in the addition in Columns 3-22 of the test compounds at 3× concentration to the cells of the assay plates. No mixing was performed in the assay wells and the signal of the emitted fluorescence was recorded for 300 seconds.

2. The samples contained in the wells of the Activator Plate were added to the corresponding wells of the Assay Plate by the FLIPR$^{TETRA}$, thus resulting in the addition in Columns 3-22 of the Assay Plate of the agonist compound in addition to the test compounds. The signal of the emitted fluorescence was recorded for 180 seconds.

Columns 1, 2, 23 and 24 were used as control. In particular: the "Max Signal Control in first injection" indicates the Cooling Agent 10 agonist response at $EC_{100}$, "Max Signal Control in the second injection" indicates the agonist at $EC_{80}$ (10 µM) in presence of pre-injected Assay buffer, the "Min Signal Control in first injection" corresponds to Assay buffer injection and "Min Signal Control in the second injection" indicates the agonist at $EC_{80}$ (20 µM) in presence of pre-injected reference antagonist Caspazepine at $IC_{100}$ (50 µM).

FIG. 3 represents a typical kinetic response graph obtained with all the compounds of Table 1.

During the Target Activation (TA) phase, the injection of the reference agonist at $EC_{80}$ gave an increase of fluorescent signal in MAX Signal control wells in which the assay buffer in CA was preinjected, while the response was completely inhibited in MIN Signal control wells due to the preinjection of the reference inhibitor Capsazepine.

The goal of the assay was to find antagonists of TRPM8 activity; to this aim the change of fluorescent signal during TA phase was measured.

Several parameters were computed and analyzed (Z' factor, Interplate variability, Intraplate variability, Day to Day variability, Antagonist Dose response and $IC_{50}$ determination, Agonist Dose response and $EC_{50}$ determination).

As for the antagonist Dose response and $IC_{50}$ determination, capsazepine (reference antagonist) was included as control and the $IC_{50}$ values of all the assayed compounds were calculated. All the compounds of the invention showed an $IC_{50}$ value<30 µM; the preferred compounds (1, 5, 6, 8, 13, 14, 25, 32, 33, 34, 35, 48, 52, 53, 55, 60) are charaterized by an $IC_{50}$ value<10 µM; the most preferred compound (1) has an $IC_{50}$ value=0.07 µM.

Example 66

Evaluation of in vivo Activity in Isovolumetric Bladder Model

Female rats were anesthetized with urethane. Ureters were ligated and sectioned. A catheter was inserted through the urinary meatus into the bladder before urethral ligature. Two protocols for testing compounds were used: intravenous (i.v.) or intravesical (i.ves.) administration.

In the first protocol, the bladder was filled by step of 100 µL of saline every 5 min until the occurrence of rhythmic bladder contractions (RBC). After a 30 min control period, compound (1) dissolved in solutol/NMP solution (2:1 w/w) at a dosage of 10 mg/kg, or vehicle were administered i.v (1 ml in 5 min) at a dosage of 10 mg/kg or vehicle were administered i.v and the resulting effect was followed for 60 min. For each group, Micturition Frequency (MF) and Amplitude of Micturition (AM) were measured during the control and treatment periods. Systemic treatment with compound (1) significantly reduced MF of about 36% in the first 30 min of the experiment. The time of inhibition of RBC was significantly higher of about 300 sec in compound (1) group compared to vehicle group (unpaired Student t-test).

In the second protocol, the bladder was filled first 3 times every 5 min with 100 µL of a solution of solutol/NMP (2.1 w/w) containing 0.756 mg of compound (1) or with 100 µL of vehicle, then with 100 µL of saline every 5 min until the occurrence of RBC. A maximal volume of 3 mL was infused. The threshold volume inducing RBC in each group was compared. At the dosage tested, compound (1) completely abolished RBC. Furthermore, the threshold volume (TV) in the group treated with compound (1) reached 3 mL without RBC occurrence whereas, in the vehicle group, RBC occurred in all rats with a mean volume of 0.7±0.09 ml. The compound did not change AM.

In both of the two above in vivo experiments, the compound resulted active in the reduction of vesical contractions by inhibition of the afferent pathways of the bladder, suggesting its efficacy in the treatment of Painful Bladder Syndrome (PBS) and Overactive Bladder (OAB).

Example 67

Selectivity Analysis

The objective of this study was to evaluate the effects in vitro of compound 1 on 3 cloned human channels expressed in HEK293 or CHO cells using the Fluo-8 calcium kit (AAT Bioquest, Inc.), and a Fluorescence Imaging Plate Reader (FLIPR$^{TETRA}$TM) instrument. The following 3 cloned human channels were evaluated in this study.

1. Cloned hTRPM8 channels (encoded by the human TRPM8 gene, stably expressed in CHO cells),
2. Cloned hTRPV1 channels (encoded by the human TRPV1 gene, stably expressed in HEK293 cells),
3. Cloned hTRPV4 channels (encoded by the human TRPV4 gene, stably expressed in CHO cells).

The effects of 5 concentrations (0.001, 0.01, 1, and 10 µM) of compound (1) were evaluated on these three TRP channels (n>3) using the following experimental procedure for each channel tested:

TRPM8

The ability of compound (1) to act as an antagonist of TRPM8 was evaluated with a calcium influx assay. Channels were activated with menthol, the positive control agonist, and the ability of test articles to inhibit this signal was examined and compared to the positive control antagonist, 2-APB. The signal elicited in the presence of the positive control agonist (10 µM menthol) was set to 100% and the signal in the presence of the positive control antagonist (200 µM 2-APB) was set to 0. The normalized % inhibition of the compound (1) is shown in Table. Values were considered significant and highlighted in yellow if the test article mean was three or more standard deviations away from the positive control agonist mean.

TRPV1

The ability of compound (1) to act as an antagonist of TRPV1 was evaluated with a calcium influx assay. The signal elicited in the presence of the positive control agonist (0.1 μM capsaicin) was set to 100% and the signal in the presence of the antagonist (5 μM ruthenium red) was set to 0. The normalized % inhibition of compound I is shown in Table. Values were considered significant and do not show any relevant inhibition of the ion channel at all the assay concentrations.

TRPV4

The ability of compound (1) to act as an antagonist of TRPV4 was evaluated with a calcium influx assay. The signal elicited in the presence of the positive control agonist (10 μM GSK1016790A) was set to 100% and the signal in the presence of the antagonist (5 μM ruthenium red) was set to 0. The normalized % inhibition of the compound 1 is shown in Table. Values were considered significant if the test article mean was three or more standard deviations away from the positive control agonist mean.

The results for each channel are summarized in the Table below.

| | | Compound 1 | | |
|---|---|---|---|---|
| Conc. (μM) | TRPM8 | $IC_{50}$ (TRPM8) | TRPV1 | TRPV4 |
| 0.001 | −25.22 | 0.07 μM | −9.14 | 13.30 |
| 0.01 | 21.38 | | 5.29 | 9.03 |
| 0.1 | 95.64 | | 2.12 | 12.25 |
| 1 | 95.64 | | 5.37 | 1.97 |
| 10 | 96.40 | | 4.90 | 85.67 |

Example 68

ADME Evaluation

The result of this evaluation is summarized in table below:

| | Metabolic stability hepatocytes (% remaining at 120 min @1 μM) | CYP (% inhibition) @10 μM | | hERG binding @10 μM | Plasma stability (% remaining) @10 μM | | $t_{1/2}$ i.v. rat (min) | Plasma Protein Binding (% @10 μM) | |
|---|---|---|---|---|---|---|---|---|---|
| rat | 5.0 | 1A2 | 98.8 | No effect | rat | 87 | 63 | rat | 97 |
| | | 2C9 | 63.1 | | | | | | |
| human | 2.6 | 2C19 | 55.3 | | human | 96 | | human | 98 |
| | | 2D6 | 100.0 | | | | | | |
| | | 3A4 | 33.3 | | | | | | |

TABLE I

| COMPOUND | FORMULA | CHEMICAL NAME |
|---|---|---|
| 1 | | 2-[(1-chloronaphthalen-2-yl)oxy]-N-(furan-2-ylmethyl)ethanaminium chloride |
| 2 | | 2-[(1-chloronaphthalen-2-yl)oxy]-N-[(5-methylfuran-2-yl)methyl]ethanaminium chloride |
| 3 | | N-[(5-chlorofuran-2-yl)methyl]-2-[(1-chloronaphthalen-2-yl)oxy]ethanaminium |
| 4 | | 2-[(1-chloronaphthalen-2-yl)oxy]-N-[(5-chlorothiophen-2-yl)methyl]ethanaminium |

TABLE I-continued

| COMPOUND | FORMULA | CHEMICAL NAME |
|---|---|---|
| 5 | 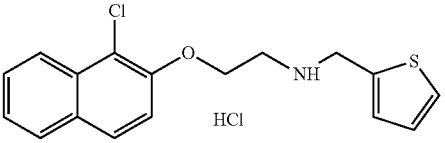 [SMILES: Clc1c(OCCNCc2cccs2)ccc2ccccc12 ; Cl] | 2-[(1-chloronaphthalen-2-yl)oxy]-N-(thiophen-2-ylmethyl)ethanaminium |
| 6 | 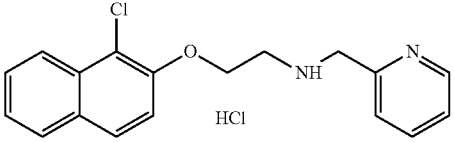 | 2-[(1-chloronaphthalen-2-yl)oxy]-N-(pyridin-2-ylmethyl)ethanaminium |
| 7 | 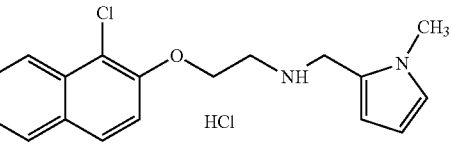 | 2-[(1-chloronaphthalen-2-yl)oxy]-N-[(1-methyl-1H-pyrrol-2-l)methyl]ethanaminium |
| 8 | 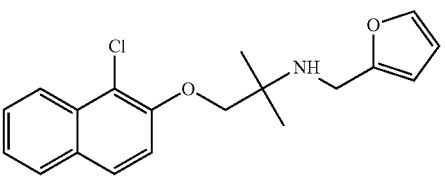 [SMILES: CC(C)(COc1ccc2ccccc2c1Cl)NCc1ccco1] | 1-[(1-chloronaphthalen-2-yl)oxy]-N-(furan-2-ylmethyl)-2-methylpropan-2-amine |
| 9 | 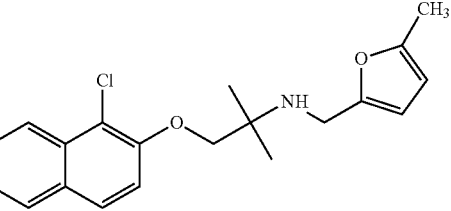 | 1-[(1-chloronaphthalen-2-yl)oxy]-2-methyl-N-[(5-methylfuran-2-yl)methyl]propan-2-amine |
| 10 | 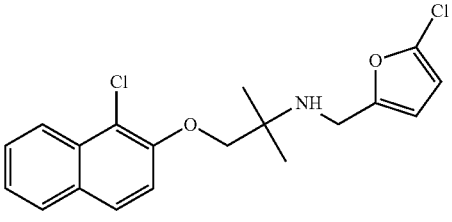 [SMILES: CC(C)(COc1ccc2ccccc2c1Cl)NCc1ccc(Cl)o1] | N-[(5-chlorofuran-2-yl)methyl]-1-[(1-chloronaphthalen-2-yl)oxy]-2-methylpropan-2-amine |
| 11 | 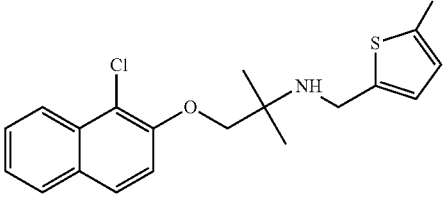 | 1-[(1-chloronaphthalen-2-yl)oxy]-N-[(5-chlorothiophen-2-yl)methyl]-2-methylpropan-2-amine |
| 12 | 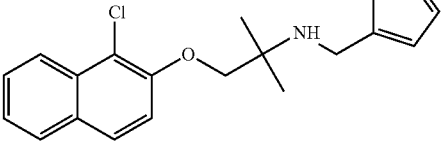 | 1-[(1-chloronaphthalen-2-yl)oxy]-2-methyl-N-(thiophen-2-ylmethyl)propan-2-amine |

TABLE I-continued

| COMPOUND | FORMULA | CHEMICAL NAME |
| --- | --- | --- |
| 13 | | 1-[(1-chloronaphthalen-2-yl)oxy]-2-methyl-N-(pyridin-2-ylmethyl)propan-2-amine |
| 14 | | 1-[(1-chloronaphthalen-2-yl)oxy]-2-methyl-N-[(1-methyl-1H-pyrrol-2-yl)methyl]propan-2-amine |
| 15 | | 2-[(1-chloronaphthalen-2-yl)oxy]-N-(furan-2-ylmethyl)propan-1-amine |
| 16 | | 2-[(1-chloronaphthalen-2-yl)oxy]-N-[(5-methylfuran-2-yl)methyl]propan-1-amine |
| 17 | | N-[(5-chlorofuran-2-yl)methyl]-2-[(1-chloronaphthalen-2-yl)oxy]propan-1-amine |
| 18 | | 2-[(1-chloronaphthalen-2-yl)oxy]-N-[(5-chlorothiophen-2-yl)methyl]propan-1-amine |
| 19 | | 2-[(1-chloronaphthalen-2-yl)oxy]-N-(thiophen-2-ylmethyl)propan-1-amine |
| 20 | | 1-[(1-chloronaphthalen-2-yl)oxy]-N-(furan-2-ylmethyl)propan-2-amine |
| 21 | | 1-[(1-chloronaphthalen-2-yl)oxy]-N-[(5-methylfuran-2-yl)methyl]propan-2-amine |

TABLE I-continued

| COMPOUND | FORMULA | CHEMICAL NAME |
|---|---|---|
| 22 | | N-[(5-chlorofuran-2-yl)methyl]-1-[(1-chloronaphthalen-2-yl)oxy]propan-2-amine |
| 23 | | 1-[(1-chloronaphthalen-2-yl)oxy]-N-[(5-chlorothiophen-2-yl)methyl]propan-2-amine |
| 24 | | 1-[(1-chloronaphthalen-2-yl)oxy]-N-(thiophen-2-ylmethyl)propan-2-amine |
| 25 | | 2-[(1-chloronaphthalen-2-yl)sulfonyl]-N-(furan-2-ylmethyl)ethanamine |
| 26 | | 2-[(1-chloronaphthalen-2-yl)sulfonyl]-N-[(5-methylfuran-2-yl)methyl]ethanamine |
| 27 | | N-[(5-chlorofuran-2-yl)methyl]-2-[(1-chloronaphthalen-2-yl)sulfonyl]ethanamine |
| 28 | | 2-[(1-chloronaphthalen-2-yl)sulfonyl]-N-[(5-chlorothiophen-2-yl)methyl]ethanamine |
| 29 | | 2-[(1-chloronaphthalen-2-yl)sulfonyl]-N-(thiophen-2-ylmethyl)ethanamine |
| 30 | | 2-[(1-chloronaphthalen-2-yl)sulfonyl]-N-(pyridin-2-ylmethyl)ethanamine |

TABLE I-continued

| COMPOUND | FORMULA | CHEMICAL NAME |
|---|---|---|
| 31 | | 2-[(1-chloronaphthalen-2-yl)sulfonyl]-N-[(1-methyl-1H-pyrrol-2-yl)methyl]ethanamine |
| 32 | | 3-(1-chloronaphthalen-2-yl)-N-(furan-2-ylmethyl)propan-1-amine |
| 33 | | 3-(1-chloronaphthalen-2-yl)-N-[(5-methylfuran-2-yl)methyl]propan-1-amine |
| 34 | | N-[(5-chlorofuran-2-yl)methyl]-3-(1-chloronaphthalen-2-yl)propan-1-amine |
| 35 | | 3-(1-chloronaphthalen-2-yl)-N-[(5-chlorothiophen-2-yl)methyl]propan-1-amine |
| 36 | | 3-(1-chloronaphthalen-2-yl)-N-(thiophen-2-ylmethyl)propan-1-amine |
| 37 | | 3-(1-chloronaphthalen-2-yl)-N-(pyridin-2-ylmethyl)propan-1-amine |
| 38 | | 2-[(1-chloronaphthalen-2-yl)oxy]-N-(furan-2-ylmethyl)-N-methylethanamine |
| 39 | | 2-[(1-chloronaphthalen-2-yl)oxy]-N-(furan-2-ylmethyl)-N,N-dimethyl-ethanaminium iodide |

TABLE I-continued

| COMPOUND | FORMULA | CHEMICAL NAME |
|---|---|---|
| 40 | 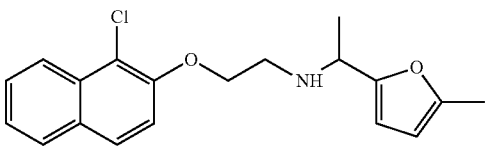 [SMILES: Cc1ccc(C(C)NCCOc2ccc3ccccc3c2Cl)o1] | N-{2-[(1-chloronaphthalen-2-yl)oxy]ethyl}-1-(5-methylfuran-2-yl)ethanamine |
| 41 | 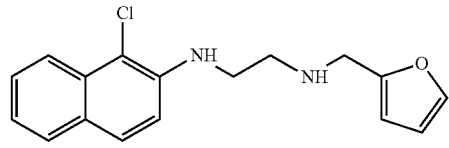 [SMILES: Clc1c(NCCNCc2ccco2)ccc2ccccc12] | N-(1-chloronaphthalen-2-yl)-N'-(furan-2-ylmethyl)ethane-1,2-diamine |
| 42 | 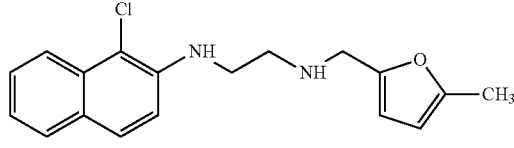 [SMILES: Cc1ccc(CNCCNc2ccc3ccccc3c2Cl)o1] | N-(1-chloronaphthalen-2-yl)-N'-[(5-methylfuran-2-yl)methyl]ethane-1,2-diamine |
| 43 | 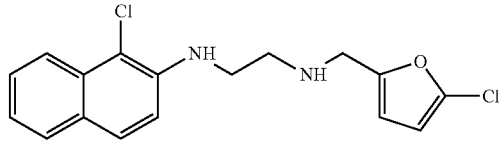 [SMILES: Clc1ccc(CNCCNc2ccc3ccccc3c2Cl)o1] | N-[(5-chlorofuran-2-yl)methyl]-N'-(1-chloronaphthalen-2-yl)ethane-1,2-diamine |
| 44 | 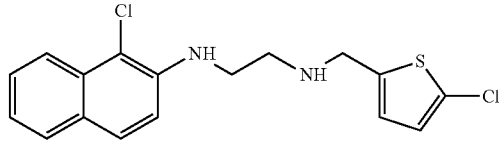 [SMILES: Clc1ccc(CNCCNc2ccc3ccccc3c2Cl)s1] | N-(1-chloronaphthalen-2-yl)-N'-[(5-chlorothiophen-2-yl)methyl]ethane-1,2-diamine |
| 45 | 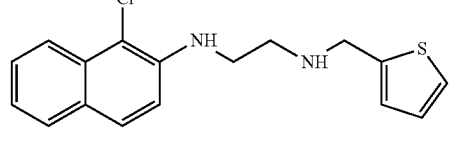 | N-(1-chloronaphthalen-2-yl)-N'-(thiophen-2-ylmethyl)ethane-1,2-diamine |
| 46 | 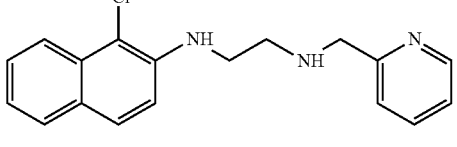 | N-(1-chloronaphthalen-2-yl)-N'-(pyridin-2-ylmethyl)ethane-1,2-diamine |
| 47 | 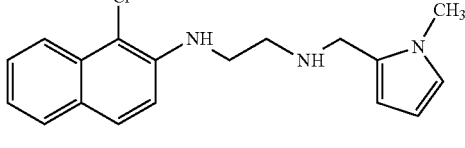 | N-(1-chloronaphthalen-2-yl)-N'-[(1-methyl-1H-pyrrol-2-yl)methyl]ethane-1,2-diamine |
| 48 | 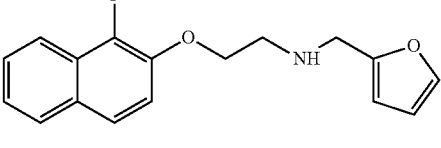 | 2-[(1-fluoronaphthalen-2-yl)oxy]-N-(furan-2-ylmethyl)ethanamine |
| 49 | 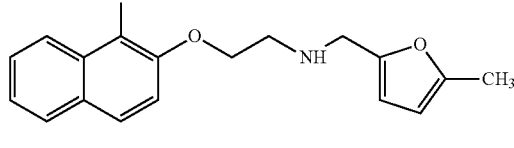 | 2-[(1-fluoronaphthalen-2-yl)oxy]-N-[(5-methylfuran-2-yl)methyl]ethanamine |

TABLE I-continued

| COMPOUND | FORMULA | CHEMICAL NAME |
|---|---|---|
| 50 | | N-[(5-chlorofuran-2-yl)methyl]-2-[(1-fluoronaphthalen-2-yl)oxy]ethanamine |
| 51 | | N-[(5-chlorothiophen-2-yl)methyl]-2-[(1-fluoronaphthalen-2-yl)oxy]ethanamine |
| 52 | | 2-[(1-fluoronaphthalen-2-yl)oxy]-N-(thiophen-2-ylmethyl)ethanamine |
| 53 | | 2-[(1-fluoronaphthalen-2-yl)oxy]-N-(pyridin-2-ylmethyl)ethanamine |
| 54 | | 2-[(1-fluoronaphthalen-2-yl)oxy]-N-[(1-methyl-1H-pyrrol-2-yl)methyl]ethanamine |
| 55 | | 5-chloro-6-{2-[(pyridin-2-ylmethyl)amino]ethoxy}naphthalene-2-carbonitrile |
| 56 | | 5-chloro-6-{2-[(furan-2-ylmethyl)amino]ethoxy}naphthalene-2-carbonitrile |
| 57 | | 5-chloro-6-(2-{[(5-methylfuran-2-yl)methyl]amino}ethoxy)naphthalene-2-carbonitrile |
| 58 | | 5-chloro-6-(2-{[(5-chlorofuran-2-yl)methyl]amino}ethoxy)naphthalene-2-carbonitrile |

TABLE I-continued

| COMPOUND | FORMULA | CHEMICAL NAME |
|---|---|---|
| 59 | | 5-chloro-6-(2-{[(5-chlorothiophen-2-yl)methyl]amino}ethoxy)naphthalene-2-carbonitrile |
| 60 | | 5-chloro-6-{2-[(thiophen-2-ylmethyl)amino]ethoxy}naphthalene-2-carbonitrile |
| 61 | | 2-[(1-ethylnaphthalen-2-yl)oxy]-N-(furan-2-ylmethyl)ethanamine |
| 62 | | 2,2-difluoro-2-[(1-fluoronaphthalen-2-yl)oxy]-N-(furan-2-ylmethyl)ethanamine |
| 63 | | 2-[(6-bromo-1-fluoronaphthalen-2-yl)oxy]-N-(furan-2-ylmethyl)ethanamine |

The invention claimed is:

1. A compound having formula (I):

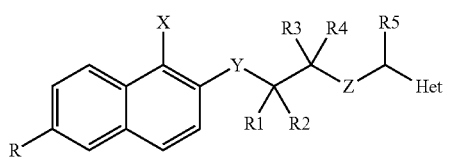

(I)

and a pharmaceutically acceptable salt thereof, wherein:

R is selected from:
  H, Br, CN, $NO_2$, $SO_2NH_2$, $SO_2NHR'$ and $SO_2N(R')_2$, where R' is selected from linear or branched $C_1$-$C_4$ alkyl;

X is selected from:
  F, Cl, $C_1$-$C_3$ alkyl, $NH_2$ and OH;

Y is selected from:
  —O—, $CH_2$, NH and $SO_2$;

R1 and R2, independently one from the other, are selected from
  H, F and linear or branched $C_1$-$C_4$ alkyl;

R3 and R4, independently one from the other, are selected from
  H and linear or branched $C_1$-$C_4$ alkyl;

Z is selected from:
  NR6 and $R6R7N^+$, where R6 and R7, independently one from the other, are selected from:
    H and linear or branched $C_1$-$C_4$ alkyl;

R5 is a residue selected from:
  H and linear or branched $C_1$-$C_4$ alkyl, and Het is a heteroaryl group selected from pyrrolyl, N-methylpyrrolyl, thiophenyl, furyl and pyridinyl, unsubstituted or substituted with one or more substituents selected from F, Cl, $CH_3$, $NH_2$ and OH.

2. The compound according to claim 1, wherein, independently one from the other:

R is selected from H, Br and CN;

X is selected from F, Cl and $C_1$-$C_3$ alkyl;

Y is selected from —O—, $CH_2$, NH and $SO_2$;

R1 and R2, independently one from the other, are selected from H, F and $CH_3$;

R3 and R4, independently one from the other, are selected from H and $CH_3$;

Z is selected from NR6 and $R6R7N^+$, where R6 and R7, independently one from the other, are selected from H and $CH_3$; and R5 is selected from H and $CH_3$.-

3. The compound according to claim 1, wherein, independently one from the other,
R is selected from H and CN;
X is selected from F and Cl;
Y is selected from $CH_2$, O and $SO_2$;
Z is selected from NH and $N^+(CH_3)_2$;
R5 is H; and
Het is substituted with at least one substituent selected from F, Cl and $CH_3$.

4. The compound according to claim 1, wherein Het is 5-substituted pyrrol-2-yl, 5-substituted N-methylpyrrol-2-yl, or 5-substituted thiophen-2-yl or 5-substituted fur-2-yl.

5. The compound according to claim 1, selected from the group consisting of:
2-[(1-chloronaphthalen-2-yl)oxy]-N-(furan-2-ylmethy) ethanaminium chloride (1);
2-[(1-chloronaphthalen-2-yl)oxy]-N-[(5-methylfuran-2-yl)methyl]ethanaminium chloride (2);
N-[(5-chlorofuran-2-yl)methyl]-2-[(1-chloronaphthalen-2-yl)oxy]ethanaminium (3);
2-[(1-chloronaphthalen-2-yl)oxy]-N-[(5-chlorothiophen-2-yl)methyl]ethanaminium (4);
2-[(1-chloronaphthalen-2-yl)oxy]-N-(thiophen-2-ylmethy)ethanaminium (5);
2-[(1-chloronaphthalen-2-yl)oxy]-N-(pyridin-2-ylmethy) ethanaminium (6);
2-[(1-chloronaphthalen-2-yl)oxy]-N-[(1-methyl-1H-pyrrol-2-yl)methyl]ethanaminium (7);
1-[(1-chloronaphthalen-2-yl)oxy]-N-(furan-2-ylmethyl)-2-methylpropan-2-amine (8);
1-[(1-chloronaphthalen-2-yl)oxy]-2-methyl-N-[(5-methylfuran-2-yl)methyl]propan-2-amine (9);
N-[(5-chlorofuran-2-yl)methyl]-1-[(1-chloronaphthalen-2-yl)oxy]-2-methylpropan-2-amine (10);
1-[(1-chloronaphthalen-2-yl)oxy]-N-[(5-chlorothiophen-2-yl)methyl]-2-methylpropan-2-amine (11);
1-[(1-chloronaphthalen-2-yl)oxy]-2-methyl-N-(thiophen-2-ylmethyl)propan-2-amin (12);
1-[(1-chloronaphthalen-2-yl)oxy]-2-methyl-N-(pyridin-2-ylmethyl)propan-2-amine (13);
1-[(1-chloronaphthalen-2-yl)oxy]-2-methyl-N- [(1-methyl-1H-pyrrol-2-yl)methyl]propan-2-amine (14);
2-[(1-chloronaphthalen-2-yl)oxy]-N-(furan-2-ylmethyl) propan-1-amine (15);
2-[(1-chloronaphthalen-2-yl)oxy]-N-[(5-methylfuran-2-yl)methyl]propan-1-amine (16);
N-[(5-chlorofuran-2-yl)methyl]-2-[(1-chloronaphthalen-2-yl)oxy]propan-1-amine (17);
2-[(1-chloronaphthalen-2-yl)oxy]-N-[(5-chlorothiophen-2-yl)methyl]propan-1-amine (18);
2-[(1-chloronaphthalen-2-yl)oxy]-N-(thiophen-2-ylmethyl)propan-1-amine (19);
1-[(1-chloronaphthalen-2-yl)oxy]-N-(furan-2-ylmethyl) propan-2-amine (20);
1-[(1-chloronaphthalen-2-yl)oxy]-N-[(5-methylfuran-2-yl)methyl]propan-2-amine (21);
N-[(5-chlorofuran-2-yl)methyl]-1-[(1-chloronaphthalen-2-yl)oxy]propan-2-amine (22);
1-[(1-chloronaphthalen-2-yl)oxy]-N-[(5-chlorothiophen-2-yl)methyl]propan-2-amine (23);
1-[(1-chloronaphthalen-2-yl)oxy]-N-(thiophen-2-ylmethyl)propan-2-amine (24);
2-[(1-chloronaphthalen-2-yl)sulfonyl]-N-(furan-2-ylmethy)ethanamine (25);
2-[(1-chloronaphthalen-2-yl)sulfonyl]-N-[(5-methylfuran-2-yl)methyl]ethanamine (26);
N-[(5-chlorofuran-2-yl)methyl]-2-[(1-chloronaphthalen-2-yl)sulfonyl]ethanamine (27);
2-[(1-chloronaphthalen-2-yl)sulfonyl]-N-[(5-chlorothiophen-2-yl)methyl]ethanamine (28);
2-[(1-chloronaphthalen-2-yl)sulfonyl]-N-(thiophen-2-ylmethy)ethanamine (29);
2-[(1-chloronaphthalen-2-yl)sulfonyl]-N-(pyridin-2-ylmethy)ethanamine (30);
2-[(1-chloronaphthalen-2-yl)sulfonyl]-N-[(1-methyl-1H-pyrrol-2-yl)methyl] ethanamine (31);
3-(1-chloronaphthalen-2-yl)-N-(furan-2-ylmethyl)propan-1-amine (32);
3-(1-chloronaphthalen-2-yl)-N-[(5-methylfuran-2-yl)methyl]propan-1-amine (33);
N-[(5-chlorofuran-2-yl)methyl]-3-(1-chloronaphthalen-2-yl)propan-1-amine (34);
3-(1-chloronaphthalen-2-yl)-N-[(5-chlorothiophen-2-yl)methyl]propan-1-amine (35);
3-(1-chloronaphthalen-2-yl)-N-(thiophen-2-ylmethyl) propan-1-amine (36);
3-(1-chloronaphthalen-2-yl)-N-(pyridin-2-ylmethyl)propan-1-amine (37);
2-[(1-chloronaphthalen-2-yl)oxy]-N-(furan-2-ylmethyl)-N-methylethanamine (38);
2-[(1-chloronaphthalen-2-yl)oxy]-N-(furan-2-ylmethyl)-N,N-dimethylethanaminium iodide (39);
N-{2-[(1-chloronaphthalen-2-yl)oxy]ethyl}-1-(5-methylfuran-2-yl)ethanamine (40);
N-(1-chloronaphthalen-2-yl)-N'-(furan-2-ylmethyl) ethane-1,2-diamine (41);
N-(1-chloronaphthalen-2-yl)-N'-[(5-methylfuran-2-yl) methyl]ethane-1,2-diamine (42);
N-[(5-chlorofuran-2-yl)methyl]-N'-(1-chloronaphthalen-2-yl)ethane-1,2-diamine (43);
N-(1-chloronaphthalen-2-yl)-N'-[(5-chlorothiophen-2-yl) methyl]ethane-1,2-diamine (44);
N-(1-chloronaphthalen-2-yl)-N'-(thiophen-2-ylmethy) ethane-1,2-diamine (45);
N-(1-chloronaphthalen-2-yl)-N'-(pyridin-2-ylmethy) ethane-1,2-diamine (46);
N-(1-chloronaphthalen-2-yl)-N'-[(1-methyl-1H-pyrrol-2-yl)methyl]ethane-1,2-diamine (47);
2-[(1-fluoronaphthalen-2-yl)oxy]-N-(furan-2-ylmethy) ethanamine (48);
2-[(1-fluoronaphthalen-2-yl)oxy]-N-[(5-methylfuran-2-yl)methyl]ethanamine (49);
N-[(5-chlorofuran-2-yl)methyl]-2-[(1-fluoronaphthalen-2-yl)oxy]ethanamine (50);
N-[(5-chlorothiophen-2-yl)methyl]-2-[(1-fluoronaphthalen-2-yl)oxy]ethanamine (51);
2-[(1-fluoronaphthalen-2-yl)oxy]-N-(thiophen-2-ylmethy)ethanamine (52);
2-[(1-fluoronaphthalen-2-yl)oxy]-N-(pyridin-2-ylmethy) ethanamine (53);
2-[(1-fluoronaphthalen-2-yl)oxy]-N-[(1-methyl-1H-pyrrol-2-yl)methyl]ethanamine (54);
5-chloro-6-{2-[(pyridin-2-ylmethyl)amino] ethoxy}naphthalene-2-carbonitrile (55);
5-chloro-6-{2-[(furan-2-ylmethyl)amino] ethoxy}naphthalene-2-carbonitrile (56);
5-chloro-6-(2-{[(5-methylfuran-2-yl)methyl] amino}ethoxy)naphthalene-2-carbonitrile (57);
5-chloro-6-(2-{[(5-chlorofuran-2-yl)methyl] amino}ethoxy)naphthalene-2-carbonitrile (58);
5-chloro-6-(2-{[(5-chlorothiophen-2-yl)methyl] amino}ethoxy)naphthalene-2-carbonitrile (59);

5-chloro-6-{2-[(thiophen-2-ylmethyl)amino]
ethoxy}naphthalene-2-carbonitrile (60);

2-[(1-ethylnaphthalen-2-yl)oxy]-N-(furan-2-ylmethy)
ethanamine (61);

2,2-difluoro-2-[(1-fluoronaphthalen-2-yl)oxy]-N-(furan-2-ylmethy)ethanamine (62); and 2-[(6-bromo-1-fluoronaphthalen-2-yl)oxy]-N-(furan-2-ylmethy)ethanamine (63).

6. The compound according to claim 1, selected from the group consisting of:
2-[(1-chloronaphthalen-2-yl)oxy]-N-(furan-2-ylmethy) ethanaminium chloride (1);
2-[(1-chloronaphthalen-2-yl)oxy]-N-(thiophen-2-ylmethy)ethanaminium (5);
2-[(1-chloronaphthalen-2-yl)oxy]-N-(pyridin-2-ylmethy) ethanaminium (6);
1-[(1-chloronaphthalen-2-yl)oxy]-N-(furan-2-ylmethyl)-2-methylpropan-2-amine (8);
1-[(1-chloronaphthalen-2-yl)oxy]-2-methyl-N-(pyridin-2-ylmethyl)propan-2-amine (13);
1-[(1-chloronaphthalen-2-yl)oxy]-2-methyl-N-[(1-methyl-1H-pyrrol-2-yl)methyl]propan-2-amine (14);
2-[(1-chloronaphthalen-2-yl)sulfonyl]-N-(furan-2-ylmethy)ethanamine (25);
3-(1-chloronaphthalen-2-yl)-N-(furan-2-ylmethyl)propan-1-amine (32);
3-(1-chloronaphthalen-2-yl)-N-[(5-methylfuran-2-yl)methyl]propan-1-amine (33);
N-[(5-chlorofuran-2-yl)methyl]-3-(1-chloronaphthalen-2-yl)propan-1-amine (34);
3-(1-chloronaphthalen-2-yl)-N-[(5-chlorothiophen-2-yl)methyl]propan-1-amine (35);
2-[(1-fluoronaphthalen-2-yl)oxy]-N-(furan-2-ylmethy) ethanamine (48);
2-[(1-fluoronaphthalen-2-yl)oxy]-N-(thiophen-2-ylmethy)ethanamine (52);
2-[(1-fluoronaphthalen-2-yl)oxy]-N-(pyridin-2-ylmethy) ethanamine (53);
5-chloro-6-{2-[(pyridin-2-ylmethyl)amino] ethoxy}naphthalene-2-carbonitrile (55); and
5-chloro-6-{2-[(thiophen-2-ylmethyl)amino] ethoxy}naphthalene-2-carbonitrile (60).

7. A pharmaceutical composition comprising as the active ingredient at least one compound according claim 1 in combination with suitable excipients and/or diluents.

8. The pharmaceutical composition according to claim 7, suitable to be administered by intravesical route, intravenous route, dermal route, oral route, and inhalatory route.

9. The pharmaceutical composition according to claim 7, in the form of a controlled release formulation.

10. A method of preventing, treating, or preventing and treating disorders, diseases, or disorders and diseases associated with the activity of the TRPM8 (Transient Receptor Potential cation channel subfamily M member 8) selected from the group consisting of: inflammatory conditions, ischaemia, pain, urological disorders, stroke, psychiatric disorders and neurodegeneration, the method comprising administering a compound according to claim 1.

11. The method according to claim 10, wherein said disorders, diseases, or disorders and diseases are selected from chronic pain, neuropathic pain, postoperative pain, osteoarthritic pain, rheumatoid arthritic pain, cancer pain, neuralgia, fibromyalgia, neuropathies, algesia, nerve injury, migraine, headaches, itch, irritable bowel syndrome and respiratory diseases, bladder syndrome, interstitial cystitis, detrusor overactivity, urinary incontinence, neurogenic detrusor overactivity, idiopathic detrusor overactivity, benign prostatic hyperplasia, lower urinary tract disorders and lower urinary tract symptoms, anxiety and depression.

12. The method of claim 11, wherein said neuropathic pain is selected from cold allodynia and diabetic neuropathic pain.

13. A process for preparing the compound according to claim 1, comprising:
reacting the aminic intermediate (IA):

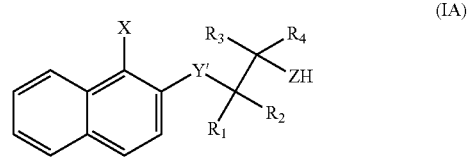

(IA)

wherein X, R1, R2, R3, R4 and Z have the same meanings as those of formula (I) and Y'=O, CH$_2$, NH and S, with R5CO-Het, wherein Het and R5 have the same meanings as those of formula (I), and subsequently adding to the reaction mixture a mild reducing agent, thereby obtaining the compound (IB):

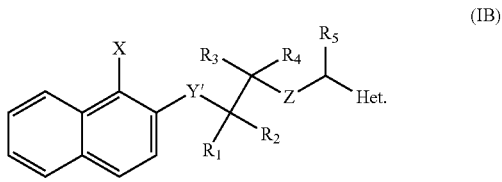

(IB)

14. The process according to claim 13, wherein the mild reducing agent is sodium borohydride.

15. The process according to claim 13, wherein the compound (IB) coincides with formula (I) when Y'=O, CH$_2$, or NH.

16. The process according to claim 13, further comprising, when Y'=S, oxidizing the compound (IB) to yield the compound of formula (I) having Y=SO$_2$.

* * * * *

UNITED STATES PATENT AND TRADEMARK OFFICE
CERTIFICATE OF CORRECTION

| | | |
|---|---|---|
| PATENT NO. | : 8,906,946 B2 | Page 1 of 2 |
| APPLICATION NO. | : 13/982235 | |
| DATED | : December 9, 2014 | |
| INVENTOR(S) | : Alessio Moriconi et al. | |

It is certified that error appears in the above-identified patent and that said Letters Patent is hereby corrected as shown below:

On the Title Page, column 2 Item 56 (Other Publications), entry 1, line 3, delete "Flourometric" and insert -- Fluorometric --.

Page 2, column 1 Item 56 (Other Publications), entry 4, line 11, delete "CBI" and insert -- CB1 --.

In the Claims

Column 54, line 67, in claim 2, delete "$CH_3$.-" and insert -- $CH_3$. --.

Column 55, line 16, in claim 5, delete "ylmethy)" and insert -- ylmethyl) --.

Column 55, lines 24-25, in claim 5, delete "ylmethy)" and insert -- ylmethyl) --.

Column 55, line 26, in claim 5, delete "ylmethy)" and insert -- ylmethyl) --.

Column 55, line 39, in claim 5, delete "amin" and insert -- amine --.

Column 55, line 42, in claim 5, delete "N- [(1" and insert -- N-[(1 --.

Column 55, lines 64-65, in claim 5, delete "ylmethy)" and insert -- ylmethyl) --.

Column 56, line 6, in claim 5, delete "methy)" and insert -- methyl) --.

Column 56, lines 7-8, in claim 5, delete "ylmethy)" and insert -- ylmethyl) --.

Column 56, line 38, in claim 5, delete "ylmethy)" and insert -- ylmethyl) --.

Column 56, line 40, in claim 5, delete "ylmethy)" and insert -- ylmethyl) --.

Signed and Sealed this
Fifth Day of May, 2015

Michelle K. Lee
*Director of the United States Patent and Trademark Office*

CERTIFICATE OF CORRECTION (continued)
U.S. Pat. No. 8,906,946 B2

Column 56, line 44, in claim 5, delete "ylmethy)" and insert -- ylmethyl) --.

Column 56, lines 52-53, in claim 5, delete "ylmethy)" and insert -- ylmethyl) --.

Column 56, line 54, in claim 5, delete "ylmethy)" and insert -- ylmethyl) --.

Column 57, line 3, in claim 5, delete "ylmethy)" and insert -- ylmethyl) --.

Column 57, line 6, in claim 5, delete "ylmethy)" and insert -- ylmethyl) --.

Column 57, line 8, in claim 5, delete "ylmethy)" and insert -- ylmethyl) --.

Column 57, line 11, in claim 6, delete "ylmethy)" and insert -- ylmethyl) --.

Column 57, lines 13-14, in claim 6, delete "ylmethy)" and insert -- ylmethyl) --.

Column 57, line 15, in claim 6, delete "ylmethy)" and insert -- ylmethyl) --.

Column 57, lines 23-24, in claim 6, delete "ylmethy)" and insert -- ylmethyl) --.

Column 57, line 33, in claim 6, delete "ylmethy)" and insert -- ylmethyl) --.

Column 57, lines 35-36, in claim 6, delete "ylmethy)" and insert -- ylmethyl) --.

Column 57, line 37, in claim 6, delete "ylmethy)" and insert -- ylmethyl) --.

Column 57, line 44, in claim 7, after "according" insert -- to --.